US011859178B2

(12) United States Patent
Gallant et al.

(10) Patent No.: US 11,859,178 B2
(45) Date of Patent: *Jan. 2, 2024

(54) NUCLEIC ACID LIBRARY METHODS

(71) Applicant: 10x Genomics, Inc., Pleasanton, CA (US)

(72) Inventors: Caroline Julie Gallant, Stockholm (SE); Marlon Stoeckius, Stockholm (SE); Katherine Pfeiffer, San Francisco, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 18/165,721

(22) Filed: Feb. 7, 2023

(65) Prior Publication Data

US 2023/0183684 A1 Jun. 15, 2023

Related U.S. Application Data

(63) Continuation of application No. 17/963,749, filed on Oct. 11, 2022, now Pat. No. 11,608,498, which is a continuation of application No. 17/690,628, filed on Mar. 9, 2022, now Pat. No. 11,512,308, which is a continuation of application No. PCT/US2021/035211, filed on Jun. 1, 2021.

(60) Provisional application No. 63/033,577, filed on Jun. 2, 2020.

(51) Int. Cl.
  *C12N 15/10* (2006.01)
  *C12Q 1/6837* (2018.01)
  *C12Q 1/6874* (2018.01)

(52) U.S. Cl.
  CPC ....... *C12N 15/1093* (2013.01); *C12Q 1/6837* (2013.01); *C12Q 1/6874* (2013.01)

(58) Field of Classification Search
  CPC .............. C12N 15/1093; C12Q 1/6837; C12Q 1/6874; C12Q 1/6806; C12Q 2563/179; C12Q 2525/307; C12Q 2525/191; C12Q 2531/113
  See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,641,658 A | 6/1997 | Adams | |
| 5,648,245 A | 7/1997 | Fire et al. | |
| 5,658,751 A | 8/1997 | Yue | |
| 5,750,341 A | 5/1998 | Macevicz | |
| 5,763,175 A | 6/1998 | Brenner | |
| 5,830,711 A | 11/1998 | Barany et al. | |
| 5,837,832 A | 11/1998 | Chee et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 6,013,440 A | 1/2000 | Lipshutz | |
| 6,027,889 A | 2/2000 | Barany et al. | |
| 6,060,240 A | 5/2000 | Kamb et al. | |
| 6,130,073 A | 10/2000 | Eggerding | |
| 6,143,496 A | 11/2000 | Brown | |
| 6,153,389 A | 11/2000 | Haarer | |
| 6,165,714 A | 12/2000 | Lane et al. | |
| 6,210,891 B1 | 4/2001 | Nyren | |
| 6,210,894 B1 | 4/2001 | Brennan | |
| 6,214,587 B1 | 4/2001 | Dattagupta | |
| 6,258,568 B1 | 7/2001 | Nyren | |
| 6,266,459 B1 | 7/2001 | Walt | |
| 6,274,320 B1 | 8/2001 | Rothberg | |
| 6,300,063 B1 | 10/2001 | Lipshutz et al. | |
| 6,309,824 B1 | 10/2001 | Drmanac | |
| 6,344,316 B1 | 2/2002 | Lockhart | |
| 6,355,431 B1 | 3/2002 | Chee | |
| 6,368,801 B1 | 4/2002 | Faruqi | |

(Continued)

FOREIGN PATENT DOCUMENTS

| | | |
|---|---|---|
| CN | 1680604 | 10/2005 |
| CN | 108676814 | 10/2018 |

(Continued)

OTHER PUBLICATIONS

U.S. Appl. No. 16/353,937, filed Mar. 14, 2019, Frisen et al.
U.S. Appl. No. 17/707,189, filed Mar. 29, 2022, Chell et al.
U.S. Appl. No. 61/902,105, filed Nov. 8, 2013, Kozlov et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.

(Continued)

*Primary Examiner* — David C Thomas
(74) *Attorney, Agent, or Firm* — Fish & Richardson P.C.

(57) ABSTRACT

Provided herein are methods, compositions, and kits for removing a portion of a sequence in a member of a nucleic acid library.

30 Claims, 10 Drawing Sheets

(56) References Cited

U.S. PATENT DOCUMENTS

| | | |
|---|---|---|
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,620,584 B1 | 9/2003 | Chee |
| 6,632,641 B1 | 10/2003 | Brennan |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,878,515 B1 | 4/2005 | Landegren |
| 6,897,023 B2 | 5/2005 | Fu |
| 6,942,968 B1 | 9/2005 | Dickinson et al. |
| 6,969,589 B2 | 11/2005 | Patil |
| 7,057,026 B2 | 6/2006 | Barnes |
| 7,115,400 B1 | 10/2006 | Adessi |
| 7,118,883 B2 | 10/2006 | Inoue |
| 7,166,431 B2 | 1/2007 | Chee et al. |
| 7,211,414 B2 | 5/2007 | Hardin |
| 7,255,994 B2 | 8/2007 | Lao |
| 7,258,976 B2 | 8/2007 | Mitsuhashi |
| 7,297,518 B2 | 11/2007 | Quake |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,582,420 B2 | 9/2009 | Oliphant et al. |
| 7,601,498 B2 | 10/2009 | Mao |
| 7,635,566 B2 | 12/2009 | Brenner |
| 7,674,752 B2 | 3/2010 | He |
| 7,700,286 B2 | 4/2010 | Stroun et al. |
| 7,709,198 B2 | 5/2010 | Luo et al. |
| 7,776,567 B2 | 8/2010 | Mao |
| 7,803,943 B2 | 9/2010 | Mao |
| 7,910,304 B2 | 3/2011 | Drmanac |
| 7,955,794 B2 | 6/2011 | Shen et al. |
| 7,960,119 B2 | 6/2011 | Chee |
| 8,003,354 B2 | 8/2011 | Shen et al. |
| 8,148,068 B2 | 4/2012 | Brenner |
| 8,206,917 B2 | 6/2012 | Chee |
| 8,288,103 B2 | 10/2012 | Oliphant |
| 8,337,851 B2 | 12/2012 | Aukerman |
| 8,460,865 B2 | 6/2013 | Chee |
| 8,481,257 B2 | 7/2013 | Van Eijk |
| RE44,596 E | 11/2013 | Stroun et al. |
| 8,603,743 B2 | 12/2013 | Liu et al. |
| 8,604,182 B2 | 12/2013 | Luo et al. |
| 8,685,889 B2 | 4/2014 | Van Eijk |
| 8,748,103 B2 | 6/2014 | Faham et al. |
| 8,815,512 B2 | 8/2014 | Van Eijk |
| 8,835,358 B2 | 9/2014 | Fodor |
| 8,911,945 B2 | 12/2014 | Van Eijk |
| 8,951,726 B2 | 2/2015 | Luo et al. |
| 9,062,348 B1 | 6/2015 | Van Eijk |
| 9,121,069 B2 | 9/2015 | Lo |
| 9,194,001 B2 | 11/2015 | Brenner |
| 9,217,176 B2 | 12/2015 | Faham |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,340,830 B2 | 5/2016 | Lipson |
| 9,371,598 B2 | 6/2016 | Chee |
| 9,506,061 B2 | 11/2016 | Brown et al. |
| 9,512,487 B2 | 12/2016 | Faham et al. |
| 9,593,365 B2 | 3/2017 | Frisen et al. |
| 9,644,204 B2 | 5/2017 | Hindson et al. |
| 9,694,361 B2 | 7/2017 | Bharadwaj |
| 9,702,004 B2 | 7/2017 | Van Eijk |
| 9,714,446 B2 | 7/2017 | Webster et al. |
| 9,727,810 B2 | 8/2017 | Fodor et al. |
| 9,777,324 B2 | 10/2017 | Van Eijk |
| 9,783,841 B2 | 10/2017 | Nolan et al. |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,049,770 B2 | 8/2018 | Madabhushi et al. |
| 10,059,990 B2 | 8/2018 | Boyden et al. |
| 10,078,895 B2 | 9/2018 | Madabhushi et al. |
| 10,196,691 B2 | 2/2019 | Harkin et al. |
| 10,208,982 B2 | 2/2019 | Bannish et al. |
| 10,221,461 B2 | 3/2019 | Robins et al. |
| 10,246,752 B2 | 4/2019 | Faham et al. |
| 10,273,541 B2 | 4/2019 | Hindson et al. |
| 10,357,771 B2 | 7/2019 | Bharadwaj |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,510,435 B2 | 12/2019 | Cai et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |

(56) References Cited

U.S. PATENT DOCUMENTS

| | | |
|---|---|---|
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 * | 3/2023 | Gallant .............. C12N 15/1093 |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 2002/0006477 A1 | 1/2002 | Shishido et al. |
| 2002/0040275 A1 | 4/2002 | Cravatt |
| 2002/0132246 A1 | 9/2002 | Kallioniemi et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0148335 A1 | 8/2003 | Shen et al. |
| 2003/0162216 A1 | 8/2003 | Gold |
| 2003/0170637 A1 | 9/2003 | Pirrung et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0002090 A1 | 1/2004 | Mayer et al. |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0096853 A1 | 5/2004 | Mayer |
| 2004/0106110 A1 | 6/2004 | Balasubramanian |
| 2005/0019776 A1 | 1/2005 | Callow et al. |
| 2005/0026188 A1 | 2/2005 | Van Kessel |
| 2005/0037362 A1 | 2/2005 | Remacle et al. |
| 2005/0037393 A1 | 2/2005 | Gunderson et al. |
| 2005/0048580 A1 | 3/2005 | Labaer |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2006/0110739 A1 | 5/2006 | Heyduk |
| 2006/0188875 A1 | 8/2006 | Cox et al. |
| 2006/0211001 A1 | 9/2006 | Yu et al. |
| 2006/0216775 A1 | 9/2006 | Burkart et al. |
| 2006/0228758 A1 | 10/2006 | Muchhal et al. |
| 2006/0263789 A1 | 11/2006 | Kincaid |
| 2007/0020640 A1 | 1/2007 | McCloskey et al. |
| 2007/0054288 A1 | 3/2007 | Su et al. |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0161029 A1 | 7/2007 | Li et al. |
| 2007/0172873 A1 | 7/2007 | Brenner et al. |
| 2007/0178503 A1 | 8/2007 | Jiang |
| 2007/0207482 A1 | 9/2007 | Church et al. |
| 2007/0254305 A1 | 11/2007 | Paik et al. |
| 2007/0269805 A1 | 11/2007 | Hogers |
| 2008/0009420 A1 | 1/2008 | Schroth et al. |
| 2008/0108804 A1 | 5/2008 | Hayashizaki et al. |
| 2008/0153086 A1 | 6/2008 | Wong |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0202998 A1 | 8/2009 | Schlumpberger et al. |
| 2009/0215633 A1 | 8/2009 | van Eijk et al. |
| 2009/0233802 A1 | 9/2009 | Bignell et al. |
| 2009/0253581 A1 | 10/2009 | van Eijk et al. |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0120097 A1 | 5/2010 | Matz et al. |
| 2010/0120098 A1 | 5/2010 | Grunenwald et al. |
| 2010/0145037 A1 | 6/2010 | Brive et al. |
| 2011/0028685 A1 | 2/2011 | Purkayastha et al. |
| 2011/0059436 A1 | 3/2011 | Hardin et al. |
| 2011/0111409 A1 | 5/2011 | Sinicropi et al. |
| 2011/0207134 A1 | 8/2011 | Faham et al. |
| 2011/0245111 A1 | 10/2011 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0252702 A1 | 10/2012 | Muratani et al. |
| 2013/0065768 A1 | 3/2013 | Zheng et al. |
| 2013/0171621 A1 | 7/2013 | Luo et al. |
| 2013/0202718 A1 | 8/2013 | Pepin et al. |
| 2013/0302801 A1 | 11/2013 | Asbury et al. |
| 2014/0066318 A1 | 3/2014 | Frisen et al. |
| 2014/0080715 A1 | 3/2014 | Lo et al. |
| 2014/0270435 A1 | 9/2014 | Dunn |
| 2014/0274731 A1 | 9/2014 | Raymond et al. |
| 2014/0296081 A1 | 10/2014 | Diehn et al. |
| 2014/0323330 A1 | 10/2014 | Glezer et al. |
| 2015/0000854 A1 | 1/2015 | Gann-Fetter et al. |
| 2015/0051085 A1 | 2/2015 | Vogelstein et al. |
| 2015/0292988 A1 | 10/2015 | Bharadwaj et al. |
| 2015/0344942 A1 | 12/2015 | Frisen et al. |
| 2016/0108458 A1 | 4/2016 | Frei et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2017/0016053 A1 | 1/2017 | Beechem et al. |
| 2017/0029875 A1 | 2/2017 | Zhang et al. |
| 2017/0067096 A1 | 3/2017 | Wassie et al. |
| 2017/0089811 A1 | 3/2017 | Tillberg et al. |
| 2017/0220733 A1 | 8/2017 | Zhuang et al. |
| 2017/0241911 A1 | 8/2017 | Rockel et al. |
| 2017/0335297 A1 | 11/2017 | Ha et al. |
| 2018/0051322 A1 | 2/2018 | Church et al. |
| 2018/0057873 A1 | 3/2018 | Zhou et al. |
| 2018/0105808 A1 | 4/2018 | Mikkelsen et al. |
| 2018/0112209 A1 | 4/2018 | Eshoo |
| 2018/0112261 A1 | 4/2018 | Van Driel et al. |
| 2018/0156784 A1 | 6/2018 | Usmani et al. |
| 2018/0180601 A1 | 6/2018 | Pedersen et al. |
| 2018/0201980 A1 | 7/2018 | Chee et al. |
| 2018/0216161 A1 | 8/2018 | Chen et al. |
| 2018/0216162 A1 | 8/2018 | Belhocine et al. |
| 2018/0245142 A1 | 8/2018 | So et al. |
| 2018/0282803 A1 | 10/2018 | Belgrader et al. |
| 2018/0291439 A1 | 10/2018 | van Eijk et al. |
| 2018/0305681 A1 | 10/2018 | Jovanovich et al. |
| 2019/0055594 A1 | 2/2019 | Samusik et al. |
| 2019/0064173 A1 | 2/2019 | Bharadwaj et al. |
| 2019/0085383 A1 | 3/2019 | Church et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |

(56) References Cited

U.S. PATENT DOCUMENTS

| | | |
|---|---|---|
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0224244 A1 | 7/2020 | Nilsson et al. |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0135010 A1 | 5/2023 | Tentori et al. |

FOREIGN PATENT DOCUMENTS

| | | |
|---|---|---|
| EP | 1923471 | 5/2008 |
| EP | 2002017 | 12/2008 |
| EP | 2881465 | 6/2015 |

(56) References Cited

FOREIGN PATENT DOCUMENTS

| | | |
|---|---|---|
| EP | 3013984 | 5/2016 |
| EP | 3511423 | 7/2019 |
| EP | 3541956 | 9/2019 |
| RU | 2145635 | 2/2000 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 2000/017390 | 3/2000 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2004/055159 | 7/2004 |
| WO | WO 2005/007814 | 1/2005 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2009/152928 | 12/2009 |
| WO | WO 2010/053587 | 5/2010 |
| WO | WO 2010/126614 | 11/2010 |
| WO | WO 2011/008502 | 1/2011 |
| WO | WO 2011/068088 | 6/2011 |
| WO | WO 2012/083225 | 6/2012 |
| WO | WO 2012/140224 | 10/2012 |
| WO | WO 2012/159089 | 11/2012 |
| WO | WO 2013/033271 | 3/2013 |
| WO | WO 2013/090390 | 6/2013 |
| WO | WO 2013/123442 | 8/2013 |
| WO | WO 2013/138510 | 9/2013 |
| WO | WO 2013/150082 | 10/2013 |
| WO | WO 2013/150083 | 10/2013 |
| WO | WO 2013/155119 | 10/2013 |
| WO | WO 2013/158936 | 10/2013 |
| WO | WO 2014/060483 | 4/2014 |
| WO | WO 2014/144713 | 9/2014 |
| WO | WO 2014/210223 | 12/2014 |
| WO | WO 2014/210225 | 12/2014 |
| WO | WO 2015/031691 | 3/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2017/019456 | 2/2017 |
| WO | WO 2017/075293 | 5/2017 |
| WO | WO 2017/096158 | 7/2017 |
| WO | WO 2017/177308 | 10/2017 |
| WO | WO 2017/192633 | 11/2017 |
| WO | WO 2018/064640 | 4/2018 |
| WO | WO 2018/085599 | 5/2018 |
| WO | WO 2018/091676 | 5/2018 |
| WO | WO 2019/068880 | 4/2019 |
| WO | WO 2019/140201 | 7/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047010 | 3/2020 |
| WO | WO 2020/053655 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/142490 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |

OTHER PUBLICATIONS

[No Author Listed], "HuSNP Mapping Assay User's Manual," Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.

(56) References Cited

OTHER PUBLICATIONS

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amgad et al., "Report on computational assessment of Tumor Infiltrating Lymphocytes from the International Immuno-Oncology Biomarker Working Group," Nature Partner Journals Breast Cancer, May 2020, 6:16, 13 pages.
Andresen et al., "Deciphering the Antibodyome—Peptide Arrays for Serum Antibody Biomarker Diagnostics," Current Proteomics, 6(1):1-12, 2009.
Armani et al, "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatial detection of fetal marker genes expressed at low level in adult human heart tissue," Scientific Reports, 2017, 7(1):12941, 10 pages.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.

Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bentley et al., "Accurate whole human genome sequencing using reversible terminator chemistry," Nature, 2008, 456(7218):53-59.
Bergenståhle et al., "Seamless integration of image and molecular analysis for spatial transcriptomics workflows," BMC Genomics, Jul. 2020, 21(1):482, 7 pages.
Bielas et al., "Human cancers express a mutator phenotype," Proc. Natl. Acad. Sci. USA, 2006, 103(48): 18238-18242.
Birney et al., "Identification and analysis of functional elements in 1% of the human genome by the Encode pilot project," Nature, 2007, 447(7146):799-816.
Blanchard et al., "High-density oligonucleotide arrays," Biosensors & Bioelectronics, 1996, 11(6-7):687-690.
Blandini et al., "Animal models of Parkinson's disease," FEBS J., Apr. 2012, 279(7):1156-66.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Cerutti et al., "Generation of sequence-specific, high affinity anti-DNA antibodies," Journal of Biological Chemistry, 2001, 276(16):12769-12773.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.

(56) References Cited

OTHER PUBLICATIONS

Chatterjee et al., "Mitochondrial DNA mutations in human cancer." Oncogene," 2006, 25(34):4663-4674.
Chen et al., "A Homogeneous, Ligase-mediated DNA diagnostic test," Genome research, 1998, 8(5):549-556.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Copeland et al., "Mitochondrial DNA Alterations in Cancer," Cancer Invest., 2002, 557-569.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dawson et al., "Animal models of neurodegenerative diseases," Nat Neurosci., Oct. 2018, 21(10):1370-1379.
Dawson et al., "Genetic animal models of Parkinson's disease," Neuron, Jun. 2010, 66(5):646-661.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
DePasquale et al., "DoubletDecon: Deconvoluting Doublets from Single-Cell RNA-Sequencing Data," Cell Rep., Nov. 5, 2019, 29(6):1718-1727.e8, 19 pages.
Drmanac et al., "Accurate sequencing by hybridization for DNA diagnostics and individual genomics," Nature Biotechnology, 16:54-58, 1998.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi—C," Trends in Biochemical Sciences, Jun. 2018, 43(6):469-478.
Eguiluz et al., "Multitissue array review: a chronological description of tissue array techniques, applications and procedures," Pathology Research and Practice, 2006, 202(8):561-568.

Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
FluidIGM, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
FluidIGM, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.
FluidIGM, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.
FluidIGM, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy," BMC Biology, 15:50, 9 pages, 2017.
GenBank Accession No. M10098.1, "Human 18S rRNA gene, complete," Aug. 3, 1993, 2 pages.
Gene@arrays[online], BeadArray Technology, available on or before Feb. 14, 2015, via Internet Archive: Wayback Machine URL <https://web.archive.org/web/20150214084616/http://geneearrays.com/services/microarrays/illumina/beadarray-technology/>, [retrieved on Jan. 30, 2020], 3 pages.
Giacomello et al., "Spatially resolved transcriptome profiling in model plant species", Nature Plants 3, 17061, 11 pages, 2017.
Gibson et al., "Enzymatic assembly of DNA molecules up to several hundred kilobases," Nat Methods., May 2009, 6(5):343-5.

(56) References Cited

OTHER PUBLICATIONS

Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gilles et al., "Single nucleotide polymorphic discrimination by an electronic dot blot assay on semiconductor microchips," Nat Biotechnol, Apr. 1999, 17(4):365-70.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging in Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goltsev et al., "Deep Profiling of Mouse Splenic Architecture with CODEX Multiplexed Imaging," Cell, 2018, 174(4):968-981.
Goransson et al., "A single molecule array for digital targeted molecular analyses," Nucleic Acids Res., Nov. 25, 2009, 37(1):e7, 9 pages.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hadley et al., "Determining composition of micron-scale protein deposits in neurodegenerative disease by spatially targeted optical microproteomics," ELIFE, 2015, 4(e09579):21 pages.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Han et al., "3C and 3C-based techniques: the powerful tools for spatial genome organization deciphering", Molecular Cytogenetics (2018) 11: 21, 10 pages, 2018.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hlubek et al, "Heterogeneous expression of Wnt/b-catenin target genes within colorectal cancer," 2007, Int. J. Cancer: 2017, 1941-1948.
Inoue and Wittbrodt, "One for All—A Highly Efficient and Versatile Method for Fluorescent Immunostaining in Fish Embryos," PLoS One 6, e19713, 2011.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Kolovos et al., "Investigation of the spatial structure and interactions of the genome at sub-kilobasepair resolution using T2C," Nat. Protoc., 2018, 13:459-477.

Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Lassmann et al., A Novel Approach for Reliable Microarray Analysis of Microdissected Tumor Cells From Formalin-Fixed and Paraffin-Embedded Colorectal Cancer Resection Specimens, J Mol Med, 87, 211-224, 2009.
Lee et al., "Fluorescent in situ sequencing (FISSEQ) of RNA for gene expression profiling in intact cells and tissues," Nature Protocols, 2015, 10(3):442-458.
Lee et al., "Identifying T Cell Receptors from High-Throughput Sequencing: Dealing with Promiscuity in TCRα and TCRβ Pairing," PLoS Comput Biol., Jan. 2017, 13(1):e1005313, 25 pages.
Lein et al., "The promise of spatial transcriptomics for neuroscience in the era of molecular cell typing", Science 358, 64-69, 2017.
Leriche et al., "Cleavable linkers in chemical biology," Bioorganic & Medicinal Chemistry, 2012, 20:571-582.
Lewczuk et al., "Cerebrospinal fluid and blood biomarkers for neurodegenerative dementias: An update of the Consensus of the Task Force on Biological Markers in Psychiatry of the World Federation of Societies of Biological Psychiatry," World J Biol Psychiatry, Jun. 2018, 19(4):244-328.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "RNase H-dependent PCR-enabled T-cell receptor sequencing for highly speci!c and ef!cient targeted sequencing of T-cell receptor mRNA for single-cell and repertoire analysis," Nature Protocols, Aug. 2019, 14:2571-2594.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lundberg et al., "Multiplexed homogeneous proximity ligation assays for high-throughput protein biomarker research in serological material," Mol Cell Proteomics, 2011, 10(4):M110.004978, 11 pages.
MacBeath et al., "Printing proteins as microarrays for high-throughput function determination," Science, Sep. 2000, 289(5485):1760-1763.

(56) References Cited

OTHER PUBLICATIONS

Maniatis et al., "Spatiotemporal Dynamics of Molecular Pathology in Amyotrophic Lateral Sclerosis", 54 pages, 2018.
Martin, "Cutadapt removes adapter sequences from high-throughput sequencing reads," EMBnet Journal, 2011, 17(1):10-12.
Marx, "Method of the Year: spatially resolved transcriptomics," Nature Methods, 2021, 18(1):9-14.
McGinnis et al., "MULTI-seq: sample multiplexing for single-cell RNA sequencing using lipid-tagged indices," Nat Methods, Jul. 2019, 16(7): 619-626, 14 pages.
McKernan et al., "Sequence and structural variation in a human genome uncovered by short-read, massively parallel ligation sequencing using two-base encoding," Genome Res., 19: 1527-41, 2009.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Nagahara et al., "Neuroprotective effects of brain-derived neurotrophic factor in rodent and primate models of Alzheimer's disease," Nat Med., Mar. 2009, 15(3):331-337.
Nam et al., "Somatic mutations and cell identity linked by Genotyping of Transcriptomes," Nature, Jul. 2019, 571(7765):355-360.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak et al., "Entering the Postgenome Era," Science, 1995, 270(5235):368-71.
Park et al., "The Estimation of Breast Cancer Disease-Probability by Difference of Individual Susceptibility," Cancer Res. Treat., Feb. 2003, 35(1):35-51, Abstract.
Paterson et al., "Cerebrospinal fluid in the differential diagnosis of Alzheimer's disease: clinical utility of an extended panel of biomarkers in a specialist cognitive clinic," Alzheimers Res Ther., Mar. 2018, 10(1):32, 11 pages.
PCT International Preliminary Report on Patentability in International Appln. No. PCT/US2021/035211, dated Dec. 6, 2022, 17 pages.
PCT International Search Report and Written Opinion in International Appln. No. PCT/US2021/035211, dated Sep. 30, 2021, 27 pages.
PCT International Search Report and Written Opinion in International Appln. No. PCT/US2021/035242, dated Sep. 2, 2021, 13 pages.
PCT Invitation to Pay Additional Fees in International Appln. No. PCT/US2021/035211, dated Oct. 12, 2021, 17 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Rajeswari et al., "Multiple pathogen biomarker detection using an encoded bead array in droplet PCR," J. Microbial Methods, Aug. 2017, 139:22-28.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rubin et al., "Whole-genome resequencing reveals loci under selection during chicken domestication.," Nature, Mar. 2010, 464: 587-591.
Salmén et al., "Barcoded solid-phase RNA capture for Spatial Transcriptomics profiling in mammalian tissue sections," Nature Protocols, Oct. 2018, 13(11):2501-2534.
Salmen et al., "Multidimensional transcriptomics provides detailed information about immune cell distribution and identity in HER2+ breast tumors," bioRxiv, 2018, 41 pages.
Saxonov et al., "10x Genomics, Mastering Biology to Advance Human Health," PowerPoint, 10x, 2020, 41 pages.
Scheideler et al., "Recapitulating complex biological signaling environments using a multiplexed, DNA-patterning approach," Sci. Adv., 2020, 6:eay5696.
Schena et al., "Quantitative monitoring of gene expression patterns with a complementary DNA microarray," Science, Oct. 1995, 270(5235):467-470.
Schmitt et al., "Detection of ultra-rare mutations by next-generation sequencing," PNAS (2012) 109:14508-14523.
Schweitzer et al., "Immunoassays with rolling circle DNA amplification: A versatile platform for ultrasensitive antigen detection," Proc. Natl. Acad. Sci. USA, May 22, 2000, 97:10113-119.

(56) References Cited

OTHER PUBLICATIONS

Segaliny et al., "Functional TCR T cell screening using single-cell droplet microfluidics†," Lab Chip, 2018, 3733-3749.
Sergeeva et al., "Display technologies: Application for the discovery of drug and gene delivery agents," Advanced Drug Delivery Reviews, 2006, 58(15):1622-1654.
Shalon et al., "A DNA microarray system for analyzing complex DNA samples using two-color fluorescent probe hybridization," Genome Res., Jul. 1996, 6(7):639-45.
Sheth et al., "Spatial metagenomic characterization of microbial biogeography in the gut," Nature Biotechnology, Aug. 2019, 37:877-883.
Shi, "Enabling large-scale pharmacogenetic studies by high-throughput mutation detection and genotyping technologies," Clin. Chem., Feb. 2001, 47(2):164-172.
Shoemaker et al., "Quantitative phenotypic analysis of yeast deletion mutants using a highly parallel molecular bar-coding strategy," Nature genetics (1996) 14:450-456.
Sievertzon et al., "Transcriptome analysis in primary neural stem cells using a tag cDNA amplification method," BMC Neuroscience, Dec. 2005, 6: 28.
Singh et al., "High-throughput targeted long-read single cell sequencing reveals the clonal and transcriptional landscape of lymphocytes," Nat Commun., Jul. 2019, 10(1):3120, 13 pages.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoeckius et al., "Cell Hashing with barcoded antibodies enables multiplexing and doublet detection for single cell genomics," Genome Biology, Dec. 19, 2018, 19: 224, 12 pages.
Strell et al., "Placing RNA in context and space—methods for spatially resolved transcriptomics," The FEBS Journal, 2019, 286(8):1468-1481.
Stuart et al., "Comprehensive Integration of Single-Cell Data," Cell, Jun. 2019, 177(7):1888-1902.
Takei et al., "Integrated Spatial Genomics Reveals Global Architecture of Single Nuclei," Nature, Jan. 27, 2021, 590(7845):344-350, 53 pages.
Tegtmeyer et al., "Alternative Interactions of the SV40 A Protein with DNA," Virology, 1981, 115:75-87.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tomita et al., "Attention-Based Deep Neural Networks for Detection of Cancerous and Precancerous Esophagus Tissue on Histopathological Slides," JAMA Network Open. Nov. 6, 2019, 2(11):e1914645, 13 pages.
Trejo et al., "Extraction-free whole transcriptome gene expression analysis of FFPE sections and histology-directed subareas of tissue," PLoS One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Wade et al., "Genome sequence, comparative analysis, and population genetics of the domestic horse.," Science., 326: 865-7, 2009.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Waxman et al., "De-regulation of common housekeeping genes in hepatocellular carcinoma," BMC Genomics, 2007, 1-9.
Willi-Monnerat et al., "Comprehensive spatiotemporal transcriptomic analyses of the ganglionic eminences demonstrate the uniqueness of its caudal subdivision," Molecular and Cellular Nueorsciences 37: 845-856, 2008.
Worthington et al., "Cloning of random oligonucleotides to create single-insert plasmid libraries," Anal Biochem, 2001, 294(2):169-175.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Xiao et al., "Direct determination of haplotypes from single DNA molecules," Nature Methods, 2009, 6(3):199-01.
Yershov et al., "DNA analysis and diagnostics on oligonucleotide microchips," Proc. Natl. Acad. Sci. USA, May 1996, 93(10):4913-4918.
Zhang et al., "Single-base mutational analysis of cancer and genetic diseases using membrane bound modified oligonucleotides," Nucleic Acids Res., Jul. 1991, 19(14):3929-33.
Zheng et al., "Massively parallel digital transcriptional profiling of single cells," Nat Commun., Jan. 16, 2017, 8:14049, 12 pages.
Zhu et al., "Reverse transcriptase template switching: a SMART approach for full-length cDNA library construction," Biotechniques, Apr. 2001, 30(4):892-897.
Zilberman et al., "Genome-wide analysis of DNA methylation patterns," Development (2007) 134: 3959-3965.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine, 2013 11(104):1-7.
Akatsuka et al., "Rapid screening of T-cell receptor (TCR) variable gene usage by multiplex PCR: Application for assessment of clonal composition," Tissue Antigens, Jan. 5, 1999, 53:122-134.
Akatsuka et al., "T cell receptor clonal diversity following allogeneic marrow grafting," Human Immunology, Jun.-Jul. 1996, 48:125-134.
Bowen et al., "Concurrent V(D)J recombination and DNA end instability increase interchromosomal trans-rearrangements in ATM-deficient thymocytes," Nucleic Acids Research, Apr. 1, 2013, 41(8):4535-4548.
Cole et al., "Complete characterization of the human immune cell transcriptome using accurate full-length cDNA sequencing," Genome Research, Apr. 2020, 30:589-601.
Davis et al., "Recent progress in the analysis of αβ T cell and B cell receptor repertoires," Current Opinion in Immunology, Aug. 2019, 59:109-114.
Efremova et al., "Immunology in the Era of Single-Cell Technologies," Annu Rev Immunol., Apr. 2020, 38:727-757.

(56) References Cited

OTHER PUBLICATIONS

Fan et al., "Single-cell RNA-seq and V(D)J profiling of immune cells in COVID-19 patients," medRxiv, May 27, 2020, 35 pages.
Heather et al., "High-throughput sequencing of the T-cell receptor repertoire: pitfalls and opportunities," Briefings in Bioinformatics, 2018, 19(4):554-565.
Hou et al., "Basic research and clinical application of immune repertoire sequencing," Int J Clin Exp Med., Oct. 30, 2016, 9(10):18868-18882.
Hudson et al., "Localization of T cell clonotypes using the Visium spatial transcriptomics platform," STAR Protocols, Jun. 17, 2022, 3:101391, 14 pages.
Kim et al., "Deep sequencing of B cell receptor repertoire," BMB Rep., Sep. 30, 2019, 52(9):540-547.
Pasetto et al., "Single-Cell TCR and Transcriptome Analysis: An Indispensable Tool for Studying T-Cell Biology and Cancer Immunotherapy," Frontiers in Immunology, Jun. 7, 2021, 12:689091, 12 pages.
Ranzoni et al., "Application of single-cell RNA sequencing methodologies in understanding haematopoiesis and immunology," Essays in Biochemistry, Jul. 3, 2019, 63:217-225.
Robins et al., "Comprehensive assessment of T-cell receptor β-chain diversity in αβ T cells," Blood, Nov. 5, 2009, 114(19):4099-4107.
Stubbington et al., "T cell fate and clonality inference from single cell transcriptomes," Nature Methods, Apr. 2016, 13(4):329-332.
Sudmeier et al., "Distinct phenotypic states and spatial distribution of CD8+ T cell clonotypes in human brain metastases," Cell Reports Medicine, May 17, 2022, 3:100620, 22 pages.
Teraguchi et al., "Methods for sequence and structural analysis of B and T cell receptor repertoires," Computational and Structural Biotechnology Journal, Jul. 17, 2020, 18:2000-2011.
Villa et al., "Partial V(D)J Recombination Activity Leads to Omenn Syndrome," Cell, May 29, 1998, 93:885-896.
Wang et al., "Molecular probes for enriching and detecting complex nucleic acid sequences," Nat Chem., Dec. 2017, 9(12):1222-1228.

\* cited by examiner

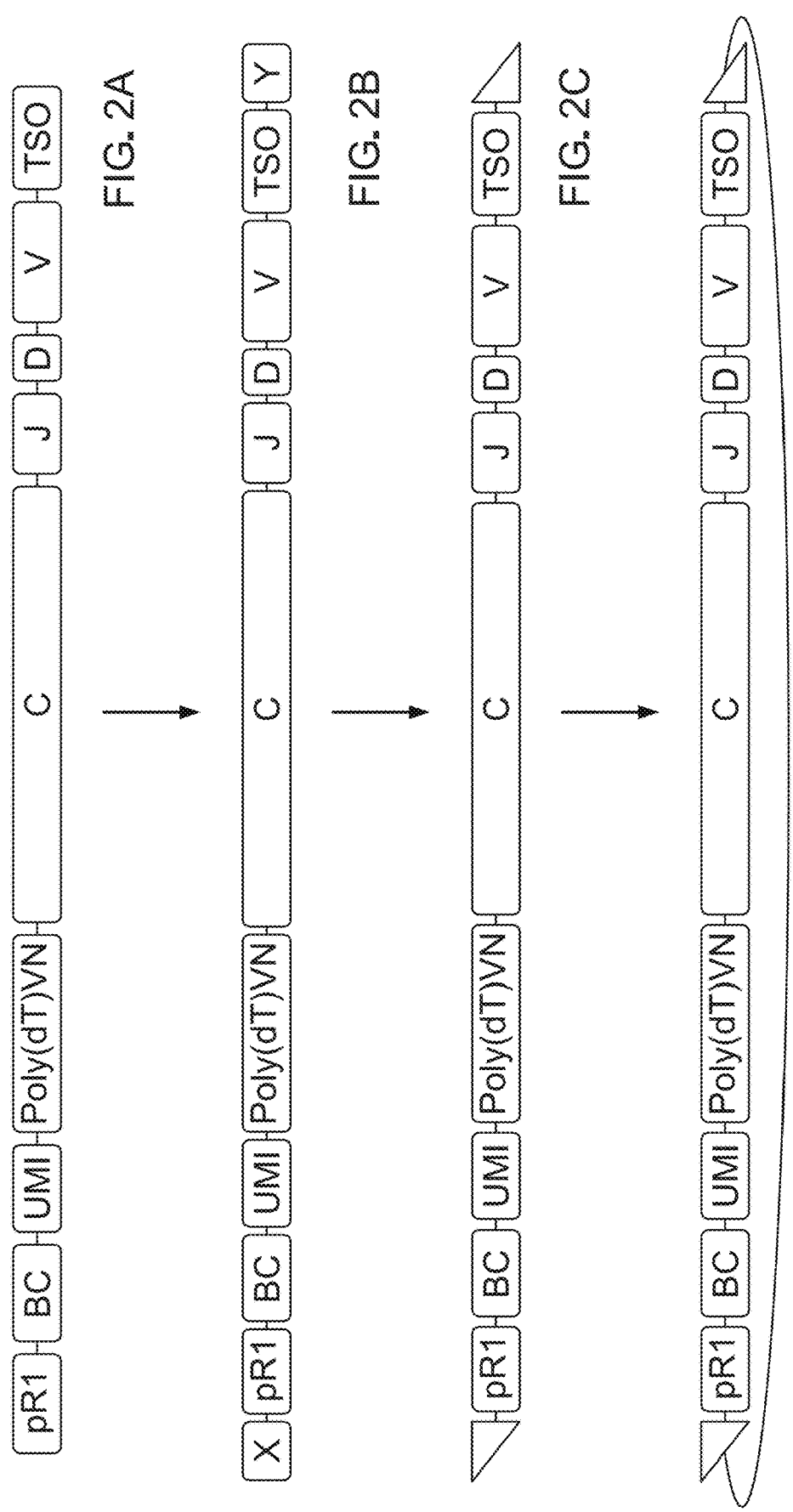

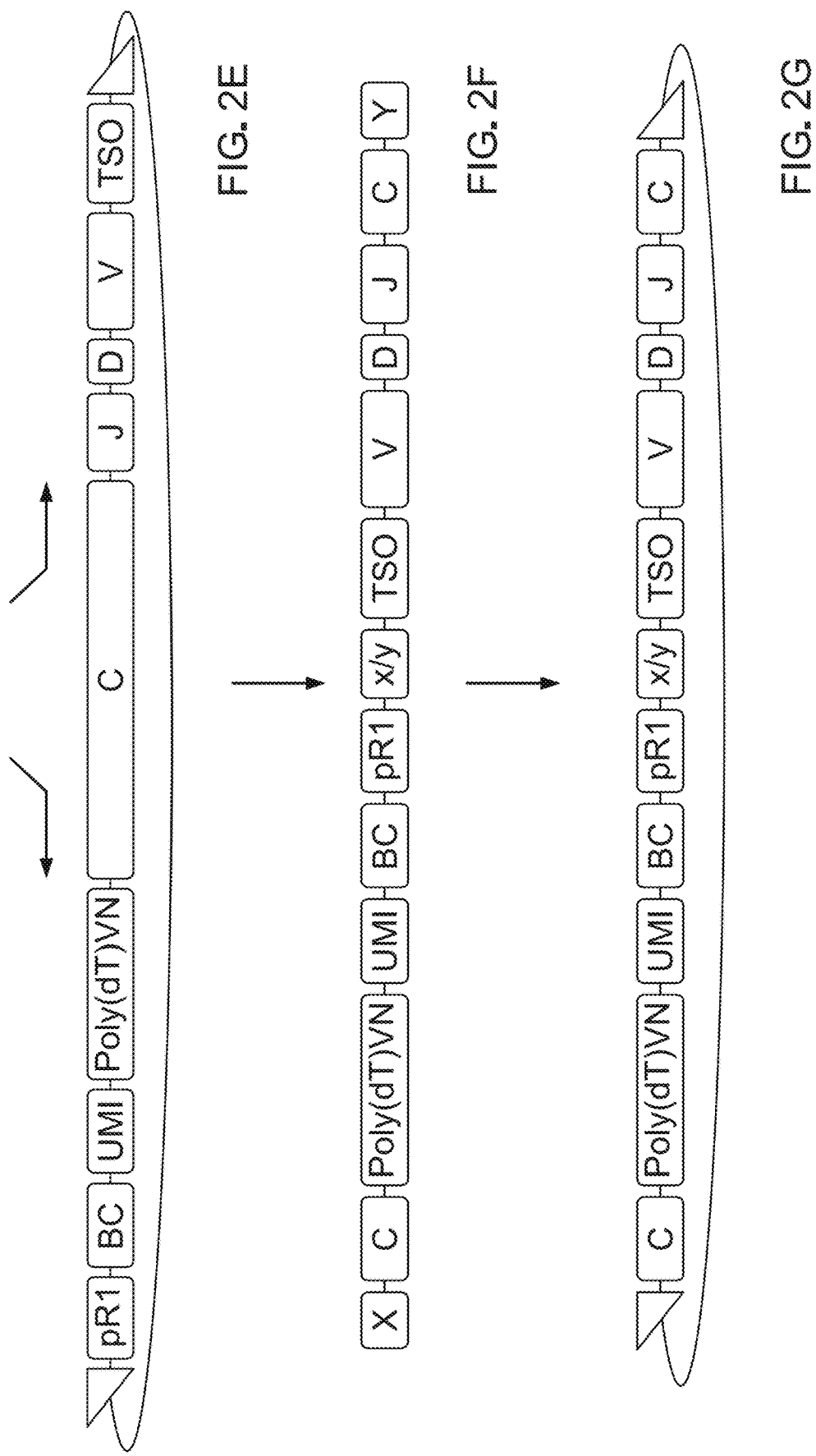

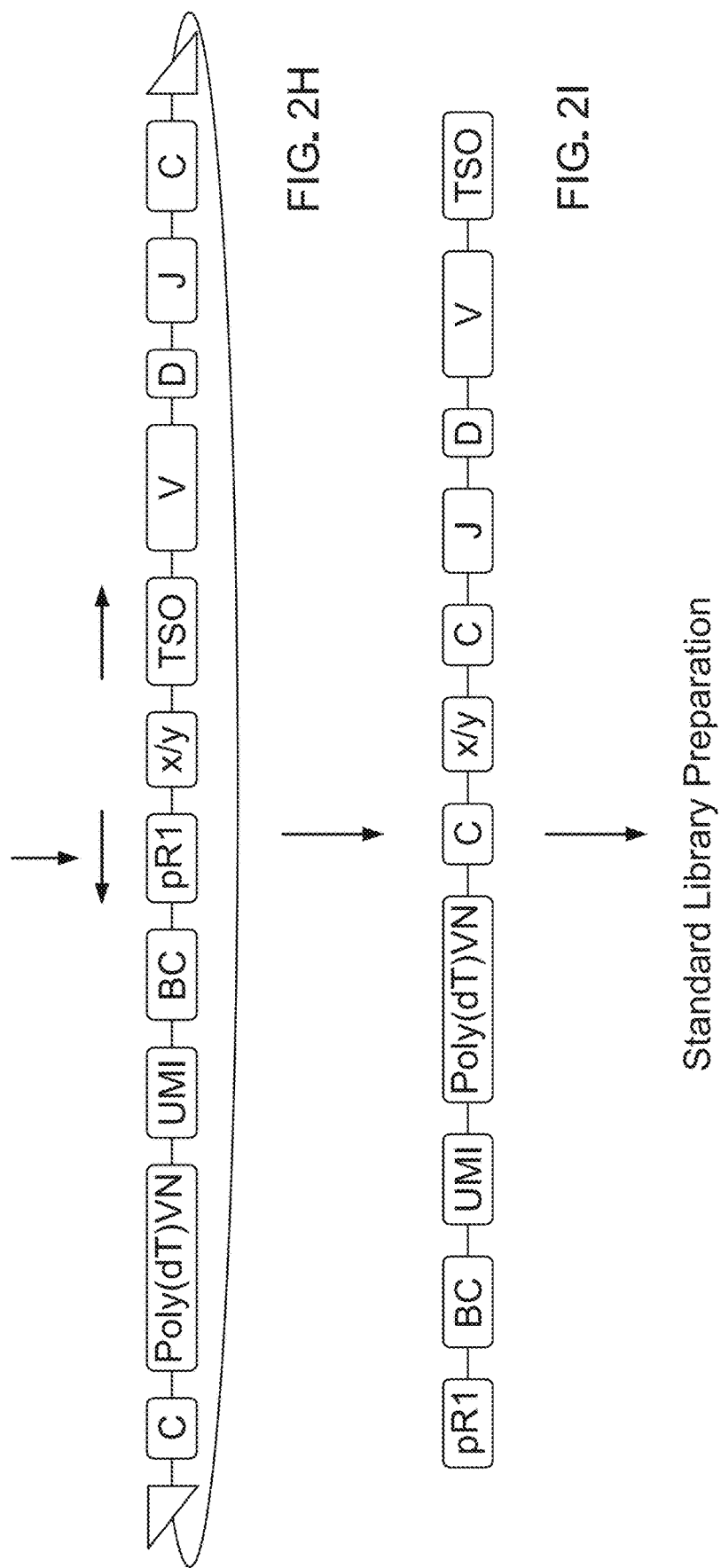

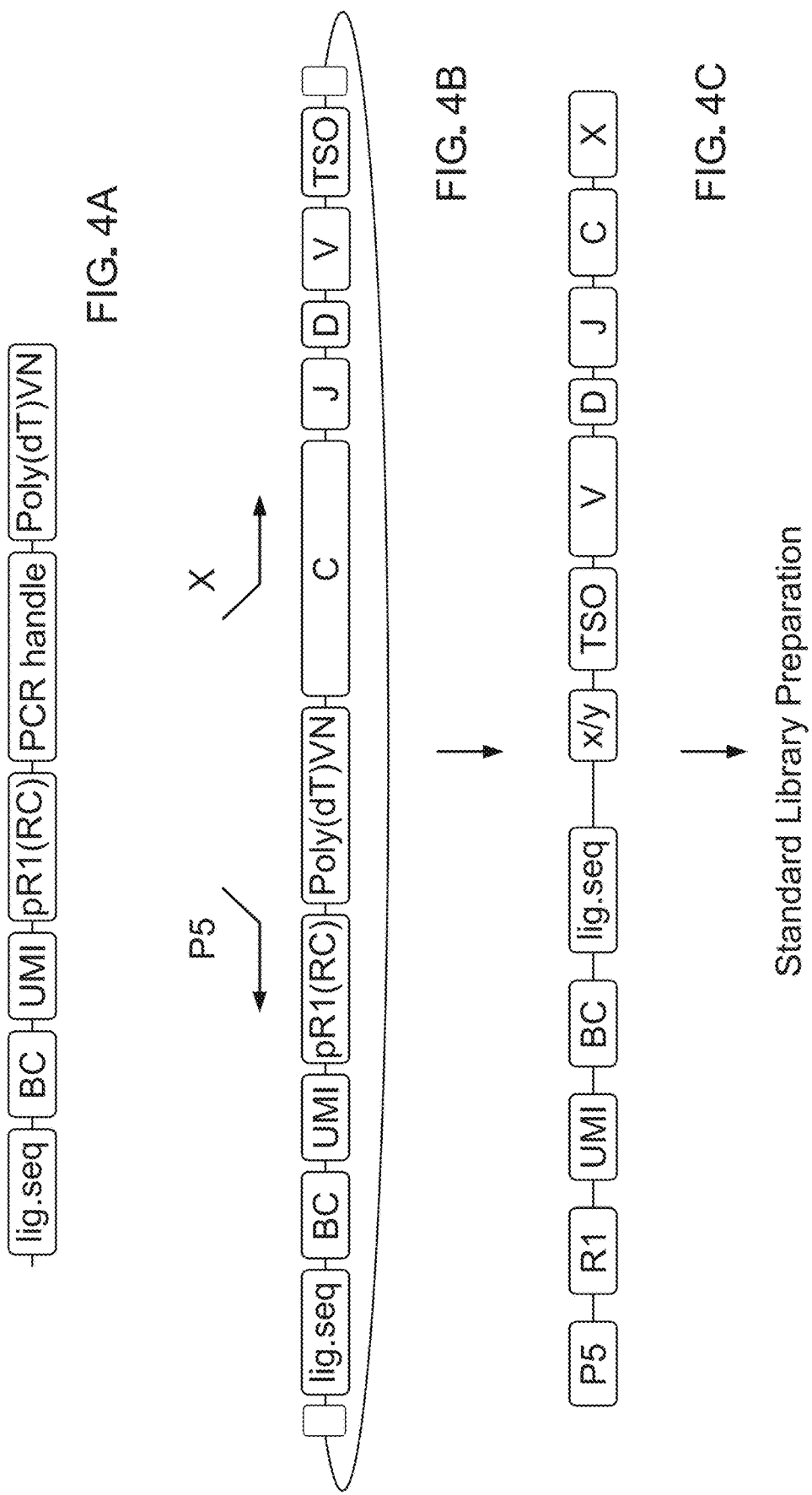

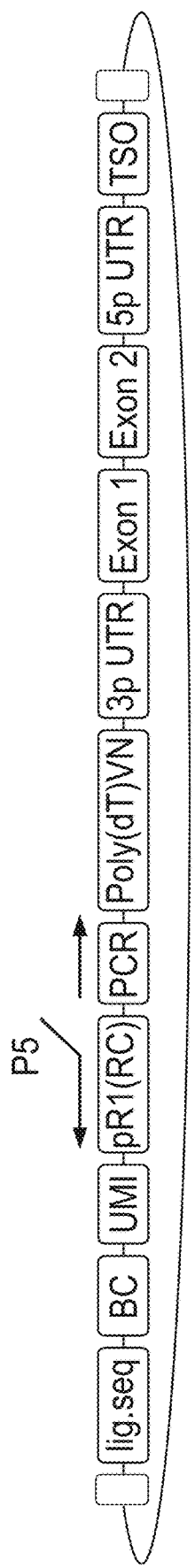
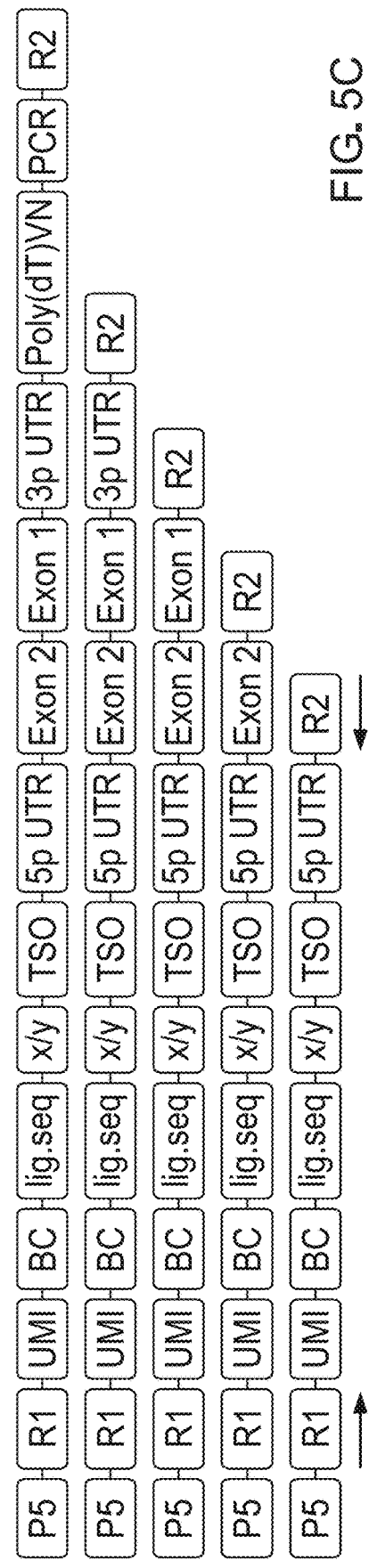
FIG. 5A
FIG. 5B
FIG. 5C

NUCLEIC ACID LIBRARY METHODS

CROSS-REFERENCE TO RELATED APPLICATIONS

This application is a continuation of U.S. patent application Ser. No. 17/963,749, filed on Oct. 11, 2022, which is a continuation of U.S. patent application Ser. No. 17/690,628, filed on Mar. 9, 2022, which is a continuation of International Application PCT/US2021/035211, with an international filing date of Jun. 1, 2021, which claims the benefit of U.S. Provisional Patent Application 63/033,577, filed on Jun. 2, 2020, the contents of which are incorporated herein by reference in its entirety.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Sequencing nucleic acid libraries generated from single-cells or spatial array analyses generally biases capture to the 3' end of captured analytes due to fragmentation and subsequent ligation of sequencing adapters. Strategies are needed to sequence regions more than about 1 kilobase away from the 3' end of analytes in nucleic acid libraries generated from single-cells or spatial array analyses.

SUMMARY

Provided herein are methods, compositions, and kits for the manipulation of nucleic acid libraries. Various methods of removing a portion of a sequence from a member of a nucleic acid library or reversing the orientation of the sequence from a member of a nucleic acid library are generally described herein. Some embodiments include double-stranded members of a nucleic acid library. Some embodiments include single-stranded members of a nucleic acid library. Some embodiments of the nucleic acid library methods provided herein remove a portion of a nucleic acid sequence in a nucleic acid library prior to standard sequencing preparation. Some embodiments of the nucleic acid library methods provided herein remove a portion of a captured analyte sequence in a nucleic acid library. Some embodiments of the nucleic acid library methods remove a portion of a constant sequence of a captured analyte. Some embodiments of the nucleic acid library methods reverse the orientation of the nucleic acid, or a portion thereof. Some embodiments of the nucleic acid library methods described herein reverse the orientation of a captured analyte, or a portion thereof. Some embodiments of the nucleic acid library methods described here include the use of nucleic acid libraries prepared from single-cells. Some embodiments of the nucleic acid libraries described herein include the use of nucleic acid libraries from arrays (e.g., a spatial array).

Thus provided herein are methods for removing all or a portion of a sequence encoding an analyte from a double-stranded member of a nucleic acid library, where the double-stranded member of the nucleic acid library includes: a first adaptor, a barcode, a capture domain, a sequence that is complementary to all or a portion of the sequence encoding the analyte, and a second adaptor, where the method includes: (a) adding to each end of the double-stranded member of the nucleic acid library a first restriction endonuclease recognition sequence; (b) contacting the double-stranded member of the nucleic acid library of step (a) with a first restriction endonuclease that cleaves the first restriction endonuclease recognition sequence at each end of the double-stranded member of the nucleic acid library; (c) ligating ends of the double-stranded member of the nucleic acid library of step (b) to generate a first double-stranded circularized nucleic acid; (d) amplifying the first double-stranded circularized nucleic acid using a first and a second primer to generate a first double-stranded nucleic acid product, where: the first primer includes: (i) a sequence substantially complementary to a 3' region of the sequence encoding the analyte and (ii) a second restriction endonuclease recognition sequence; and the second primer includes: (i) a sequence substantially complementary to a sequence from a 5' region of the sequence encoding the analyte, and (ii) the second restriction endonuclease recognition sequence; (e) contacting the first double-stranded nucleic acid product with a second restriction endonuclease that cleaves the second restriction endonuclease recognition sequence at each end of the first double-stranded nucleic acid product; (f) ligating ends of the first double-stranded nucleic acid product of step (e) to generate a second double-stranded circularized nucleic acid; and (g) amplifying the second double-stranded circularized nucleic acid using a third primer including a sequence that is substantially complementary to the first adapter and a fourth primer including a sequence that is substantially complementary to the second adapter, to generate a version of the double-stranded member of the nucleic acid library lacking all or a portion the sequence encoding the analyte.

In some embodiments, the analyte includes a sequence encoding a constant region of the analyte.

In some embodiments, the double-stranded member of the nucleic acid library includes the first adaptor, the barcode, the capture domain, the sequence that is complementary to all or a portion of the sequence encoding the constant region of the analyte, and the second adaptor, in a 5' to 3' direction.

In some embodiments, the double-stranded member of the nucleic acid library includes a UMI disposed between the barcode and the capture domain.

In some embodiments, the first primer includes (i) the sequence from the 3' region of the sequence encoding the constant region of the analyte and (ii) the second restriction endonuclease recognition sequence, in a 3' to 5' direction.

In some embodiments, the second primer includes (i) the sequence substantially complementary to the sequence from the 5' region of the sequence encoding the constant region of the analyte, and (ii) the second restriction endonuclease recognition sequence, in a 3' to 5' direction.

In some embodiments, the ligating in step (c) and/or step (f) is performed using a ligase or using template mediated ligation. In some embodiments, the ligase is a DNA ligase, where the DNA ligase is optionally T4 ligase.

In some embodiments, the barcode is a cell barcode or a spatial barcode.

In some embodiments, the nucleic acid library is a DNA library or a cDNA library.

In some embodiments, the double-stranded member of a nucleic acid library includes a sequence that is complementary to all or a portion of a sequence encoding a variable region of the analyte.

In some embodiments, the sequence that is complementary to all or a portion of the sequence encoding the constant region of the analyte is positioned 5' relative to the sequence that is complementary to all or a portion of the sequence encoding the variable region of the analyte.

In some embodiments, the sequence that is complementary to all or a portion of the sequence encoding the constant region of the analyte is positioned 3' relative to the sequence that is complementary to all or a portion of the sequence encoding the variable region of the analyte.

In some embodiments, the analyte is an immune cell receptor.

In some embodiments, the immune cell receptor is a B cell receptor. In some embodiments, the B cell receptor is an immunoglobulin kappa light chain and where the variable region of the analyte includes a CDR3 of the immunoglobulin kappa light chain, or where the variable region of the analyte includes or one both of CDR1 and CDR2 of the immunoglobulin kappa light chain, or where the variable region of the analyte includes a full-length variable domain of the immunoglobulin kappa light chain. In some embodiments, the B cell receptor is an immunoglobulin lambda light chain, and where the variable region of the analyte includes a CDR3 of the immunoglobulin lambda light chain, or where the variable region of the analyte includes one or both of CDR1 and CDR2 or the immunoglobulin lambda light chain, or where the variable region of the analyte includes a full-length variable domain of the immunoglobulin lambda light chain. In some embodiments, the B cell receptor is an immunoglobulin heavy chain, and where the variable region of the analyte includes a CDR3 of the immunoglobulin heavy chain, or where the variable region of the analyte includes one or both of CDR1 and CDR2 of the immunoglobulin heavy chain, or where the variable region of the analyte includes a full-length variable domain of the immunoglobulin heavy chain.

In some embodiments, the immune cell receptor is a T cell receptor. In some embodiments, the T cell receptor is a T cell receptor alpha chain and where the variable region of the analyte includes a CDR3 of the T cell receptor alpha chain, or where the variable region of the analyte includes one or both of CDR1 and CDR2 of the T cell receptor alpha chain, or where the variable region of the analyte includes a full-length variable domain of the T cell receptor alpha chain. In some embodiments, the T cell receptor is a T cell receptor beta chain and where the variable region of the analyte includes a CDR3 of the T cell receptor beta chain, or where the variable region of the analyte includes one or both of CDR1 and CDR2 of the T cell receptor beta chain, or where the variable region of the analyte includes a full-length variable domain of the T cell receptor beta chain.

In some embodiments, the method includes: (h) determining (i) all or a portion of a sequence encoding the variable region of the analyte or a complement thereof, and (ii) all or a portion of the barcode or a complement thereof. In some embodiments, the determining in step (h) includes sequencing (i) all or a portion of the sequence encoding the variable region of the analyte or a complement thereof, and (ii) all or a portion of the barcode or a complement thereof.

In some embodiments, the analyte was released from a biological sample, and the method includes: determining a location of the analyte in the biological sample using the determined sequences of (i) and (ii).

In some embodiments, the method includes generating the double-stranded member of the nucleic acid library. In some embodiments, the step of generating the double-stranded member of the nucleic acid library includes: contacting the analyte with a capture probe including the first adaptor, the barcode, and the capture domain, where the capture domain binds specifically to a sequence present in the analyte; extending an end of the capture probe using the analyte specifically bound to the capture domain as a template, thereby generating an extended capture probe; and adding the second adaptor an end of the extended capture probe, thereby generating the double-stranded member of the nucleic acid library.

In some embodiments, the capture probe includes the first adapter, the barcode, and the capture domain in a 5' to a 3' direction. In some embodiments, a 3' end of the capture probe is extended. In some embodiments, the second adapter is added to a 5' end of the extended capture probe.

In some embodiments, the biological sample is a tissue sample, a tissue section or a fixed tissue section, and optionally, where the fixed tissue section is formalin-fixed paraffin-embedded tissue section or the tissue section is a fresh, frozen tissue section.

In some embodiments, the analyte is an RNA, an mRNA, a DNA, or genomic DNA.

Also provided herein are kits including: (i) a first restriction endonuclease that cleaves a first restriction endonuclease recognition sequence; (ii) a second restriction endonuclease that cleaves a second restriction endonuclease recognition sequence; (iii) a ligase; and (iv) a first and a second primer, where: the first primer includes: (i) a sequence from a 3' region of a sequence encoding a constant region of an analyte and (ii) the second restriction endonuclease recognition sequence; and the second primer includes: (i) a sequence substantially complementary to a sequence from a 5' region of the sequence encoding the constant region of the analyte, and (ii) the second restriction endonuclease recognition sequence.

Also provided herein are methods for removing all or a portion of a sequence encoding an analyte from a double-stranded member of a nucleic acid library, where the double-stranded member of the nucleic acid library includes: a first adaptor, a barcode, a capture domain, a sequence that is complementary to all or a portion of the sequence encoding the analyte, and a second adaptor, where the method includes: (a) adding to each end of the double-stranded member of the nucleic acid library a first restriction endonuclease recognition sequence; (b) contacting the double-stranded member of the nucleic acid library of step (a) with a first restriction endonuclease that cleaves the first restriction endonuclease recognition sequence at each end; (c) ligating ends of the double-stranded member of the nucleic acid library of step (b) to generate a first-double-stranded nucleic circularized nucleic acid; and (d) amplifying the double-stranded circularized nucleic acid using a first primer and a second primer to generate a version of the double-stranded member of the nucleic acid library lacking all, or a portion of, the sequence encoding the analyte, where: the first primer includes: (i) a sequence substantially complementary to a sequence from a 3' region of the sequence encoding the analyte, and (ii) a sequence including a first functional domain; and the second primer includes: (i) a sequence substantially complementary to a sequence from a region of the sequence encoding the analyte, and (ii) a sequence including a second functional domain.

In some embodiments, the analyte includes a sequence encoding a constant region.

In some embodiments, the double-stranded member of the nucleic acid library includes the first adaptor, the barcode, the capture domain, the sequence complementary to all or a portion of the sequence encoding the constant region of the analyte, and the second adaptor, in a 5' to 3' direction.

In some embodiments, the double-stranded member of the nucleic acid library includes a unique molecular identifier (UMI) disposed between the spatial barcode and the capture domain.

In some embodiments, the first primer includes (i) the sequence from the 3' region of the sequence encoding the constant region of the analyte, and (ii) the sequence including the first functional domain, in 3' to 5' direction; and where the second primer includes (i) the sequence from the 5' region of the sequence encoding the constant region of the analyte, and (ii) the sequence including the second functional domain, in a 3' to 5' direction.

In some embodiments, the barcode is a spatial barcode or a cell barcode.

In some embodiments, ligating in step (c) is performed using a DNA ligase or using template mediated ligation. In some embodiments, the DNA ligase is T4 ligase.

In some embodiments, the nucleic acid library is a DNA library or a cDNA library.

In some embodiments, the double-stranded member of the nucleic acid library includes a sequence that is complementary to all or a portion of a sequence encoding a variable region of an analyte.

In some embodiments, the sequence complementary to all or a portion of the sequence encoding the constant region of the analyte is positioned 5' relative to the sequence that is complementary to all or a portion of the sequence encoding the variable regions of the analyte.

In some embodiments, the sequence complementary to all or a portion of the sequence encoding the constant region of the analyte is positioned 3' relative to the sequence that is complementary to all or a portion of the sequence encoding the variable region of the analyte.

In some embodiments, the analyte is an immune cell receptor.

In some embodiments, the immune cell receptor is a B cell receptor. In some embodiments, the B cell receptor is an immunoglobulin kappa light chain and where the variable region of the analyte includes a CDR3 of the immunoglobulin kappa light chain, or where the variable region of the analyte includes one or both of CDR1 and CDR2 of the immunoglobulin kappa light chain, or where the variable region of the analyte includes a full-length variable domain of the immunoglobulin kappa light chain. In some embodiments, the B cell receptor is an immunoglobulin lambda light chain and where the variable region of the analyte includes a CDR3 of the immunoglobulin kappa light chain, or where the variable region of the analyte includes one or both of CDR1 and CDR2 of the immunoglobulin kappa light chain, or where the variable region of the analyte includes a full-length variable domain of the immunoglobulin lambda light chain. In some embodiments, the B cell receptor is an immunoglobulin heavy chain. In some embodiments, the variable region of the analyte includes a CDR3 of the immunoglobulin heavy chain, and where the variable region of the analyte includes one or both of CDR1 and CDR2 of the immunoglobulin heavy chain, or where the variable region of the analyte includes a full-length variable domain of the immunoglobulin heavy chain.

In some embodiments, the immune cell receptor is a T cell receptor. In some embodiments, the T cell receptor is a T cell receptor alpha chain and where the variable region of the analyte includes a CDR3 of the T cell receptor alpha chain, or where the variable region of the analyte includes one or both of CDR1 and CDR2 of the T cell receptor alpha chain, or where the variable region of the analyte includes a full-length variable domain of the T cell receptor alpha chain. In some embodiments, the T cell receptor is a T cell receptor beta chain and where the variable region of the analyte includes a CDR3 of the T cell receptor beta chain, or where the variable region of the analyte includes one or both of CDR1 and CDR2 of the T cell receptor beta chain, or where the variable region of the analyte includes a full-length variable domain of the T cell receptor beta chain.

In some embodiments, the method includes amplifying the version of the double-stranded member of the nucleic acid library lacking all, or a portion of, the sequence encoding the constant region of the analyte using a third primer and fourth primer, where: the third primer is substantially complementary to the first functional domain, and the fourth primer is substantially complementary to the second functional domain.

In some embodiments, the method includes: determining (i) all or a portion of the sequence encoding the variable region of the analyte or complement thereof, and (ii) all or a portion of the sequence of the barcode or complement thereof. In some embodiments, determining the sequence includes sequencing (i) all or a portion of the sequence encoding the variable region of the analyte or a complement thereof, and (ii) all or a portion of the sequence of the barcode or a complement thereof.

In some embodiments, the sequencing is performed by sequence by synthesis, sequence by ligation or sequence by hybridization.

In some embodiments, the analyte was released from a biological sample, and the method includes: determining the location of the analyte in the biological sample using the determined sequence of (i) and (ii).

In some embodiments, the method includes generating the double-stranded member of the nucleic acid library.

In some embodiments, the step of generating the double-stranded member of the nucleic acid library includes: contacting the analyte with a capture probe including the first adaptor, the barcode, and the capture domain, where the capture domain binds specifically to a sequence present in the analyte; extending an end of the capture probe using the analyte specifically bound to the capture domain as a template, thereby generating an extended capture probe; and adding the second adaptor to an end of the extended capture probe, thereby generating the double-stranded member of the nucleic acid library.

In some embodiments, the capture probe includes the first adapter, the barcode, and the capture domain in a 5' to a 3' direction. In some embodiments, a 3' end of the capture probe is extended. In some embodiments, the second adapter is added to a 5' end of the extended capture probe.

In some embodiments, the biological sample is a tissue sample, a tissue section or a fixed tissue section, and optionally, where the fixed tissue section is formalin-fixed paraffin-embedded tissue section or a fresh, frozen tissue section.

In some embodiments, the analyte is an RNA, an mRNA, DNA, or genomic DNA.

Also provided herein are kits including: (i) a first restriction endonuclease that cleaves a first restriction endonuclease recognition sequence; (ii) a ligase; and (iii) a first and a second primer, where: the first primer includes: (i) a sequence from a 3' region of a sequence encoding a constant region of an analyte, and (ii) a sequence including a first functional domain; and the second primer includes: (i) a sequence substantially complementary to a sequence from a 5' region of a sequence encoding the constant region of the analyte, and (ii) a sequence including a second functional domain.

Also provided herein are methods for removing all or a portion of the sequence encoding an analyte from a double-stranded member of a nucleic acid library, where the double-stranded member of the nucleic acid library includes a ligation sequence, a barcode, a reverse complement of a first adaptor, a capture domain, a sequence that is complementary to all or a portion of the sequence encoding the analyte, and a second adaptor, where the method includes: ligating ends of the double-stranded member using the ligation sequence to splint ligation, to generate a circularized double-stranded nucleic acid; amplifying the circularized double-stranded nucleic acid using a first primer and a second primer to generate a version of the double-stranded member of the nucleic acid library lacking all, or a portion of, the sequence encoding the analyte, where: the first primer includes: (i) a sequence substantially complementary to the reverse complement of the first adaptor and (ii) a first functional domain; and the second primer includes: (i) a sequence substantially complementary to a sequence from a 5' region of the sequence encoding the analyte, and (ii) a second functional domain.

In some embodiments, the analyte includes a sequence encoding a constant region of the analyte.

In some embodiments, the double-stranded member of the nucleic acid library includes the ligation sequence, the barcode, the reverse complement of the first adaptor, the capture domain, the sequence complementary to all or a portion of the sequence encoding the constant region of the analyte, and the second adaptor, in a 5' to 3' direction.

In some embodiments, the double-stranded member of the nucleic acid library includes a unique molecular identifier (UMI) disposed between the barcode and the reverse complement of the first adaptor.

In some embodiments, the first primer includes (i) the sequence substantially complementary to the reverse complement of the first adaptor, and (ii) the sequence including the first functional domain, in 3' to 5' direction; and where the second primer includes (i) the sequence substantially complementary to a sequence of the 5' region of the sequence encoding the constant region of the analyte, and (ii) the sequence including the second functional domain, in a 3' to 5' direction.

In some embodiments, ligating in step (a) is performed using a DNA ligase, where the DNA ligase is T4 ligase.

In some embodiments, the barcode is a spatial barcode or a cell barcode.

In some embodiments, the nucleic acid library is a DNA library or a cDNA library.

In some embodiments, the double-stranded member of the nucleic acid library includes a sequence that is complementary to all or a portion of a sequence encoding a variable region of an analyte.

In some embodiments, the sequence complementary to all or a portion of the sequence encoding the constant region of the analyte is positioned 5' relative to the sequence that is complementary to all or a portion of the sequence encoding the variable regions of the analyte.

In some embodiments, the sequence complementary to all or a portion of the sequence encoding the constant region of the analyte is positioned 3' relative to the sequence that is complementary to all or a portion of the sequence encoding the variable region of the analyte.

In some embodiments, the analyte is an immune cell receptor.

In some embodiments, the immune cell receptor is a B cell receptor. In some embodiments, the B cell receptor is an immunoglobulin kappa light chain and where the variable region of the analyte includes a CDR3 of the immunoglobulin kappa light chain, or where the variable region of the analyte includes one or both of CDR1 and CDR2 of the immunoglobulin kappa light chain, or where the variable region of the analyte includes a full-length variable domain of the immunoglobulin kappa light chain. In some embodiments, the B cell receptor is an immunoglobulin lambda light chain and where the variable region of the analyte includes a CDR3 of the immunoglobulin kappa light chain, or where the variable region of the analyte includes one or both of CDR1 and CDR2 of the immunoglobulin kappa light chain, or where the variable region of the analyte includes a full-length variable domain of the immunoglobulin lambda light chain. In some embodiments, the B cell receptor is an immunoglobulin heavy chain and where the variable region of the analyte includes a CDR3 of the immunoglobulin heavy chain, or where the variable region of the analyte includes one or both of CDR1 and CDR2 of the immunoglobulin heavy chain, or where the variable region of the analyte includes a full-length variable domain of the immunoglobulin heavy chain.

In some embodiments, the immune cell receptor is a T cell receptor. In some embodiments, the T cell receptor is a T cell receptor alpha chain and where the variable region of the analyte includes a CDR3 of the T cell receptor alpha chain, or where the variable region of the analyte includes one or both of CDR1 and CDR2 of the T cell receptor alpha chain, or where the variable region of the analyte includes a full-length variable domain of the T cell receptor alpha chain. In some embodiments, the T cell receptor is a T cell receptor beta chain and where the variable region of the analyte includes a CDR3 of the T cell receptor beta chain, or where the variable region of the analyte includes one or both of CDR1 and CDR2 of the T cell receptor beta chain, or where the variable region of the analyte includes a full-length variable domain of the T cell receptor beta chain.

In some embodiments, the method includes amplifying the version of the double-stranded member of the nucleic acid library lacking all, or a portion of, the sequence encoding the constant region of the analyte using a third primer and fourth primer, where: the third primer is substantially complementary to the first functional domain, and the fourth primer is substantially complementary to the second functional domain.

In some embodiments, the method includes: determining (i) all or a portion of the sequence encoding the variable region of the analyte or complement thereof, and (ii) all or a portion of the sequence of the barcode or complement thereof. In some embodiments, the determining the sequence includes sequencing (i) all or a portion of the sequence encoding the variable region of the analyte or a complement thereof, and (ii) all or a portion of the sequence of the barcode or a complement thereof.

In some embodiments, the sequencing is performed using sequence by synthesis, sequence by ligation or sequence by hybridization.

In some embodiments, the analyte was released from a biological sample, and the method includes: determining the location of the analyte in the biological sample using the determined sequence of (i) and (ii).

In some embodiments, the method includes generating the double-stranded member of the nucleic acid library.

In some embodiments, the step of generating the double-stranded member of the nucleic acid library includes: contacting the analyte with a capture probe including the ligation sequence, the barcode, the reverse complement of the first adaptor, the capture domain a sequence that is complementary to all or a portion of the sequence encoding the constant region of the analyte, and a second adaptor, where the capture domain binds specifically to a sequence present in the analyte; extending an end of the capture probe using the analyte specifically bound to the capture domain as a template, thereby generating an extended capture probe; and adding the second adaptor to an end of the extended capture probe, thereby generating the double-stranded member of the nucleic acid library.

In some embodiments, the capture probe includes the ligation sequence, the barcode, the reverse complement of the first adaptor, and the capture domain in a 5' to a 3' direction. In some embodiments, a 3' end of the capture probe is extended. In some embodiments, the second adapter is added to a 5' end of the extended capture probe.

In some embodiments, the biological sample is a tissue sample, a tissue section, or a fixed tissue section, and optionally, where the fixed tissue section is formalin-fixed paraffin-embedded tissue section or the tissue section is a fresh, frozen tissue section.

In some embodiments, the analyte is an RNA, an mRNA, DNA, or genomic DNA.

Also provided herein are kits including: (i) a first restriction endonuclease that cleaves a first restriction endonuclease recognition sequence; (ii) a ligase; and (iii) a first and a second primer, where: the first primer includes: (i) a sequence substantially complementary to a reverse complement of a first adaptor, and (ii) a sequence including a first functional domain; and the second primer includes: (i) a sequence substantially complementary to a sequence from a 5' region of a sequence encoding the constant region of the analyte, and (ii) a sequence including a second functional domain.

Also provided herein are methods of reversing the orientation of an analyte sequence of a double-stranded member of a nucleic acid library, where the double-stranded member of the nucleic acid library includes a ligation sequence, a barcode, a reverse complement of the first adaptor, an amplification domain, a capture domain, a sequence that is complementary to all or a portion of the sequence encoding the analyte, and a second adaptor, where the method includes: (a) ligating ends of the double-stranded member of the nucleic acid library using the ligation sequence to splint ligation, to generate a circularized double-stranded nucleic acid; and (b) amplifying the circularized double-stranded nucleic acid using a first primer and a second primer to generate a double-stranded nucleic acid product, where: the first primer includes (i) a sequence substantially complementary to the reverse complement of the first adaptor and (ii) a functional domain; and the second primer includes a sequence substantially complementary to the amplification domain, thereby reversing the orientation of the analyte sequence of the double-stranded member of the nucleic acid library.

In some embodiments, the double-stranded member of the nucleic acid library includes the ligation sequence, the barcode, the reverse complement of the first adaptor, the amplification domain, the capture domain, the sequence complementary to all or a portion of the sequence encoding an analyte, and the second adaptor, in a 5' to 3' direction.

In some embodiments, the double-stranded member of the nucleic acid library includes a unique molecular identifier (UMI) disposed between the barcode and the reverse complement of the first adaptor.

In some embodiments, the first primer includes (i) the sequence substantially complementary to the reverse complement of the first adaptor, and (ii) the sequence including the first functional domain, in a 5' to 3' direction.

In some embodiments, ligating in step (a) is performed using a ligase. In some embodiments, the ligase is a DNA ligase, where the DNA ligase is T4 ligase.

In some embodiments, the barcode is a spatial barcode or a cell barcode.

In some embodiments, the nucleic acid library is a DNA library or a cDNA library.

In some embodiments, the double-stranded member of the nucleic acid library includes a sequence that is complementary to all or a portion of a sequence encoding a 5' untranslated region of an analyte.

In some embodiments, the double-stranded member of the nucleic acid library includes a sequence that is complementary to all or a portion of a sequence encoding a 3' untranslated region of an analyte.

In some embodiments, the sequence that is complementary to all or a portion of the sequence encoding a 5' untranslated region of the analyte is positioned 5' relative to the sequence that is complementary to all or a portion of the sequence encoding the 3' untranslated region of the analyte.

In some embodiments, the double-stranded member of the nucleic acid library includes one or more exons of the analyte.

In some embodiments, the analyte includes the sequence that is complementary to all or a portion of the sequence encoding the 5' untranslated region of the analyte, the one or more exons, and the sequence that is complementary to all or a portion of the sequence encoding the 3' untranslated region, in a 5' to 3' direction.

In some embodiments, the method includes: (c) determining (i) all or a portion of a sequence encoding the analyte or a complement thereof, and (ii) all or a portion of the barcode, or a complement thereof. In some embodiments, the determining in step (c) includes sequencing (i) all or a portion of the sequence encoding the analyte or a complement thereof, and (ii) all or a portion of the barcode or a complement thereof.

In some embodiments, the sequencing includes high throughput sequencing performed using sequence by synthesis, sequence by ligation or sequence by hybridization.

In some embodiments, the analyte was released from a biological sample, and the method includes: determining a location of the analyte in the biological sample using the determined sequences of (i) and (ii).

In some embodiments, the method includes generating the double-stranded member of the nucleic acid library.

In some embodiments, the step of generating the double-stranded member of the nucleic acid library includes: contacting the analyte with a capture probe including the ligation sequence, the barcode, the reverse complement of the first adaptor, the amplification domain, and the capture domain, where the capture domain binds specifically to a sequence present in the analyte; extending an end of the capture probe using the analyte specifically bound to the capture domain as a template, thereby generating an extended capture probe; and adding the second adaptor to an end of the extended capture probe, thereby generating the double-stranded member of the nucleic acid library.

In some embodiments, the capture probe includes the ligation sequence, the barcode, the reverse complement of the first adaptor, the amplification domain, and the capture domain in a 5' to a 3' direction. In some embodiments, a 3' end of the capture probe is extended. In some embodiments, the second adapter is added to a 5' end of the extended capture domain.

In some embodiments, the biological sample is a tissue sample, a tissue section or a fixed tissue section, and optionally, where the fixed tissue section is formalin-fixed paraffin-embedded tissue section or the tissue section is a fresh, frozen tissue section.

In some embodiments, the analyte is an RNA, an mRNA, DNA, or genomic DNA.

In some embodiments, the analyte is a nucleic acid encoding an immune cell receptor.

In some embodiments, where the immune cell receptor is a B-cell receptor and where the B cell receptor is one of an immunoglobulin kappa light chain, an immunoglobulin lambda chain, and/or an immunoglobulin heavy chain.

In some embodiments, the immune cell receptor is a T cell receptor and where the T cell receptor is one or both of a T cell receptor alpha chain and a T cell receptor beta chain.

Also provided herein are kits including: (i) a first restriction endonuclease that cleaves a first restriction endonuclease recognition sequence; (ii) a ligase; and (iii) a first and a second primer, where: the first primer includes: (i) a sequence substantially complementary to a reverse complement of a first adaptor, and (ii) a functional domain; and the second primer includes a sequence substantially complementary to the amplification domain.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 2A-I show an exemplary nucleic acid library preparation workflow.

FIGS. 4A-D show an exemplary nucleic acid library preparation workflow.

FIGS. 5A-C show an exemplary nucleic acid library preparation workflow.

DETAILED DESCRIPTION

Figure 1:
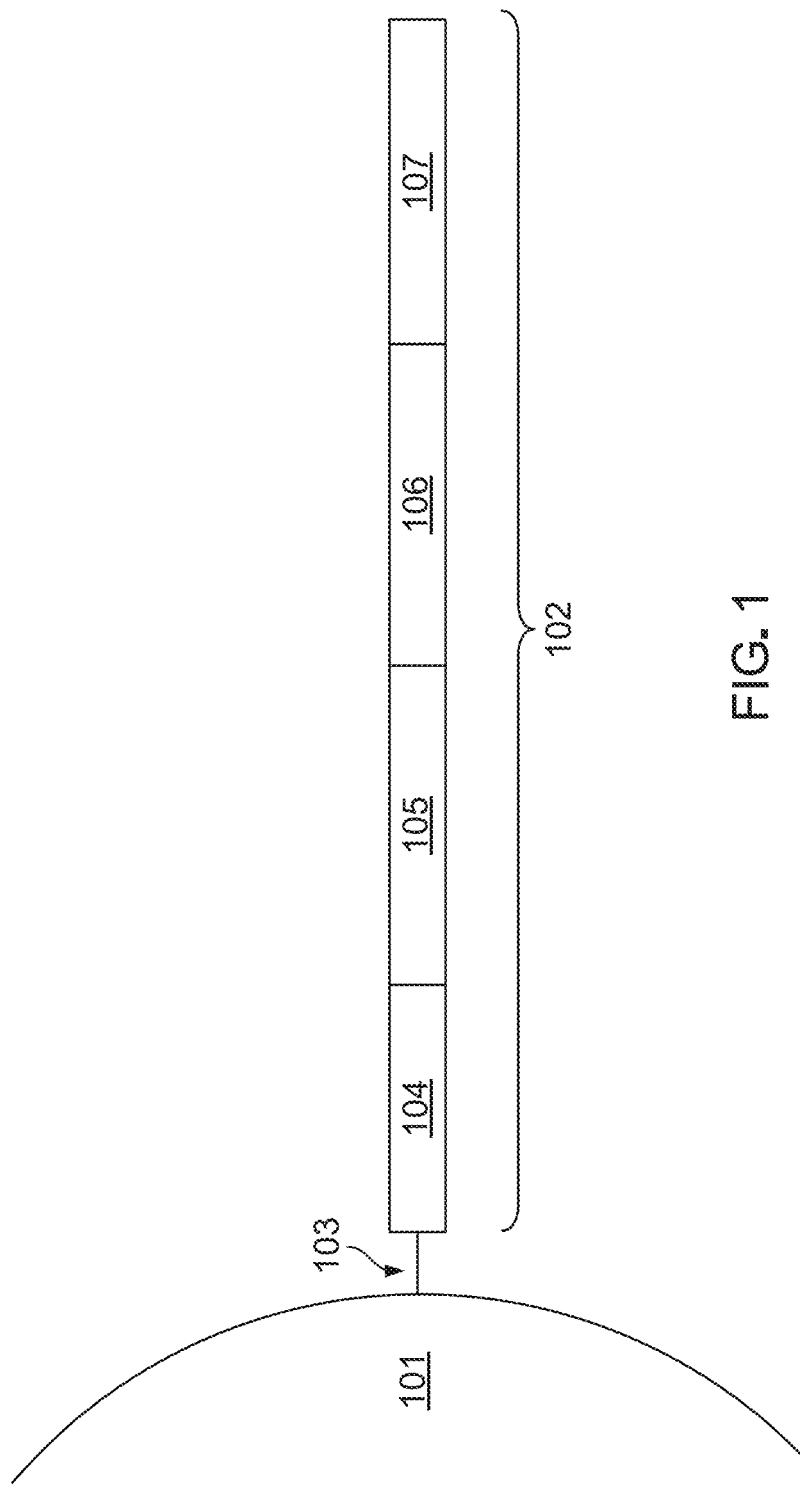
FIG. 1 shows a schematic diagram showing an exemplary barcoded capture probe, as described herein.

Sequencing nucleic acid libraries generated from single-cells or spatial array analyses generally biases capture to the 3' end of captured analytes due to fragmentation and subsequent ligation of sequencing adapters. Strategies are needed to sequence regions more than about 1 kilobase away from the 3' end of analytes in nucleic acid libraries generated from single-cells or spatial array analyses.

Provided herein are methods, compositions, and kits for the manipulation of nucleic acid libraries. Various methods of removing a portion of a sequence from a member of a nucleic acid library or reversing the orientation of the sequence from a member of a nucleic acid library are generally described herein. Some embodiments include double-stranded members of a nucleic acid library. Some embodiments include single-stranded members of a nucleic acid library. Some embodiments of the nucleic acid library methods provided herein remove a portion of a nucleic acid sequence in a nucleic acid library prior to standard sequencing preparation. Some embodiments of the nucleic acid library methods provided herein remove a portion of a captured analyte sequence in a nucleic acid library. Some embodiments of the nucleic acid library methods remove a portion of a constant sequence of a captured analyte. Some embodiments of the nucleic acid library methods reverse the orientation of the nucleic acid, or a portion thereof. Some embodiments of the nucleic acid library methods described herein reverse the orientation of a captured analyte, or a portion thereof. Some embodiments of the nucleic acid library methods described here include the use of nucleic acid libraries prepared from single-cells. Some embodiments of the nucleic acid libraries described herein include the use of nucleic acid libraries from arrays (e.g., a spatial array).

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774, 374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10x Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligation products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Methods for Preparing Nucleic Acid Libraries

Sequencing nucleic acid libraries generated from single-cell or spatial array analyses generally biases capture to the 3' end of captured analytes due to fragmentation and ligation of sequencing adapters. Alternative nucleic acid library preparation strategies described herein allow sequencing of regions further away (e.g., 5') from the 3' end of analytes in nucleic acid libraries. The 5' analyte sequence enrichment strategies described herein assist in the identification (e.g., sequencing) of critical sequences (e.g., V(D)J sequences, CDR sequences) important in understanding immune cell receptor clonality in health and disease. For example, nucleic acid libraries (e.g., cDNA libraries) generated in single-cell analysis and arrays, (e.g., spatial arrays described herein), are generally biased to sequences from the 3' end and as a result sequences more than about 1 kb away from the end of a poly(A) tail are generally not present in the sequencing library, thereby making it difficult to study 5' coding regions and non-coding regions (e.g., 5' untranslated region (UTR)) of analytes beyond 1 kb from the end of the poly(A) tail). In some examples described herein, the nucleic acid libraries are generated from single-cell assay systems. In some examples described herein, nucleic acid libraries are generated from array (e.g., spatial array) based assay systems.

Provided herein are methods, compositions, and kits for the manipulation of nucleic acid libraries. Various methods of removing a portion of a sequence from a member of a nucleic acid library or reversing the orientation of the sequence from a member of a nucleic acid library are generally described herein. Some embodiments include double-stranded members of a nucleic acid library. Some embodiments include single-stranded members of a nucleic acid library. Some embodiments of the nucleic acid library methods provided herein remove a portion of a nucleic acid sequence in a nucleic acid library prior to standard sequencing preparation. Some embodiments of the nucleic acid library methods provided herein remove a portion of a captured analyte sequence in a nucleic acid library. Some embodiments of the nucleic acid library methods remove a portion of a constant sequence of a captured analyte. Some embodiments of the nucleic acid library methods reverse the orientation of the nucleic acid, or a portion thereof. Some embodiments of the nucleic acid library methods described herein reverse the orientation of a captured analyte, or a portion thereof. Some embodiments of the nucleic acid library methods described here include the use of nucleic acid libraries prepared from single-cells. Some embodiments of the nucleic acid libraries described herein include the use of nucleic acid libraries from arrays (e.g., a spatial array).

An example of sequences of interest beyond 1 kb from the end of the poly(A) include, but are not limited to, sequences encoding T-cell receptors (TCRs) and B-cell receptor (BCR) immunoglobulins. Most T-cell receptors are generally composed of a variable alpha chain and a variable beta chain. T-cell receptor genes include multiple V (variable), D (diversity), and J (joining) gene segments in their alpha and beta chains that are rearranged during the development of the lymphocyte to provide the cell with a unique antigen receptor. Similarly, B-cell receptor genes contain multiple V, D, and J gene segments encoding a membrane-bound immunoglobulin molecule of the following isotypes IgD, IgM, IgA, IgG, or IgE. V(D)J sequences from both TCRs and BCRs also include complementarity determining region(s) (CDRs), such as CDR1, CDR 2, and CDR3, which provide specificity to the antigen-binding regions.

Generally described herein are preparation methods for nucleic acid libraries. In some embodiments, the nucleic acid library is a DNA library. In some embodiments, the nucleic acid library is a cDNA library. In some embodiments, the nucleic acid library is a double-stranded nucleic acid library. In some embodiments, the nucleic acid library is a single-stranded nucleic acid library. The nucleic acid preparation methods described herein describe various steps, including ligation. In some embodiments ligation includes using a ligase (e.g. any of the ligases described herein). In some embodiments, the ligase is a DNA ligase. In some embodiments, the ligase is T4 ligase. In some embodiments, the ligase is CircLigase.

In some embodiments of the nucleic acid preparation methods described herein, a member of a nucleic acid library is circularized. In some embodiments, a member of a nucleic acid library is circularized two times. In some embodiments, a double-stranded member of a nucleic acid library is circularized. In some embodiments, a single-stranded member of a nucleic acid library is circularized. Any suitable method to circularize a member of a nucleic acid library can be used, including the examples described herein. In some embodiments, a member of a nucleic acid library is circularized to bring 5' sequences of interest closer to domains positioned at the 3' end of the member of a nucleic acid library. In some embodiments, the 5' sequences of interest are brought closer to domains (e.g., circularized), such as a unique molecular identifier and a barcode sequence (e.g., a cell barcode, a spatial barcode). In some embodiments, the 5' sequences of interest are brought closer to domains positioned at the 3' end by the methods described in Naml, A. S., Somatic mutation and cell identify linked by Genotyping of Transcriptomes, *Nature*, 571, 355-360 (2019), which is incorporated herein by reference in its entirety.

In some examples, a single-stranded member of a nucleic acid library is circularized after contacting the member with an enzyme to phosphorylate a 5' end of a single-stranded member of the nucleic acid library (e.g., polynucleotide kinase). In some embodiments, the phosphorylated single-stranded member of a nucleic acid library can be circularized with CircLigase. In some embodiments, the single-stranded member can be circularized by a templated ligation reaction (e.g., splint ligation). In some embodiments, a splint oligonucleotide can facilitate the ligation reaction where the splint oligonucleotide is complementary to both ends of a linear single stranded member of a nucleic acid library such that hybridization of the splint oligonucleotide to both ends brings the two ends in proximity for a ligation reaction to occur.

In some examples, a single-stranded member of a nucleic acid library is amplified with a phosphorylated primer (e.g., a phosphorylated pR1 primer). In some embodiments, the amplicons are denatured to generate single-stranded members of the nucleic acid library. In some embodiments, a splint oligonucleotide can facilitate the ligation reaction as previously described.

In some examples, a double-stranded member of a nucleic acid library can be circularized by a Gibson assembly strategy (Gibson, D. G., Enzymatic assembly of DNA molecules up to several hundred kilobases, *Nature Methods*, 6(5): 343-345, doi:10.1038/nmeth.1318 (2009), which is incorporated herein by reference in its entirety). In some embodiments, homologous sequences are designed on either end (e.g., a 3' end, a 5' end) of the amplified molecule (e.g., a cDNA molecule). In some embodiments, Gibson assembly of the double stranded product generates a circularized double-stranded member of a nucleic acid library.

In some examples, restriction enzyme (e.g., restriction endonucleases) recognition sites can be added to the ends of a member of a nucleic acid, digested with a restriction enzyme, and intramolecularly ligated to generate a circularized nucleic acid product. Any suitable restriction enzyme can be used. In some embodiments, a rare restriction enzyme can be used. As used herein, a "rare restriction enzyme" is a restriction enzyme with a recognition sequence that occurs only rarely in a genome. For example, rare restriction enzymes with a 7-nucleotide recognition site cut once every $4^7$ bp (16,384 bp), and those with 8-nucleotide recognition sites cut every $4^8$ bp (65,536 bp), respectively. Use of a rare restriction enzyme recognition site in a nucleic acid for subsequence cleavage and circularization could be useful, for example, to help minimize unwanted cleavage within the target nucleic acid which could occur with a restriction enzyme recognition site that is more prevalent within a genome.

In some embodiments, a member of a nucleic acid library is circularized by Cre-Lox recombination. In some embodiments, a member (e.g., single-stranded) of a nucleic acid library is circularized by CircLigase™ ligation enzyme.

As used herein, a "barcode" is a label, or identifier, that conveys or is capable of conveying information (e.g., information about an analyte in a sample, a bead, and/or a capture probe). For example, a barcode can be associated with a location in a biological sample (e.g., a spatial barcode) or a barcode can be associated with one or more cells, or a single-cell (e.g., a cell barcode). In some embodiments of the nucleic acid library preparation methods described herein, the barcode is a spatial barcode. In some embodiments of the nucleic acid library preparation methods described herein, the barcode is a cell barcode.

Provided herein are methods for removing all or a portion of a sequence encoding a constant region of an analyte from a double-stranded member of a nucleic acid library, where the double-stranded member of the nucleic acid library includes a first adaptor, a barcode, a capture domain, a sequence that is complementary to all or a portion of the sequence encoding the constant region of the analyte, and a second adaptor, where the method includes (a) adding to each end of the double-stranded member of the nucleic acid library a first restriction endonuclease recognition sequence, (b) contacting the double-stranded member of the nucleic acid library of step (a) with a first restriction endonuclease that cleaves the first restriction endonuclease recognition sequence at each end of the double-stranded member of the nucleic acid library, (c) ligating the cleaved ends of the double-stranded member of the nucleic acid library of step (b) to generate a first double-stranded circularized nucleic acid, (d) amplifying the first double-stranded circularized nucleic acid using a first and a second primer to generate a first double-stranded nucleic acid product, where the first primer includes (i) a sequence substantially complementary from a 3' region of the sequence encoding the constant region of the analyte and (ii) a second restriction endonuclease recognition sequence and the second primer includes (i) a sequence substantially complementary to a sequence from a 5' region of the sequence encoding the constant region of the analyte, and (ii) the second restriction endonuclease recognition sequence, (e) contacting the first double-stranded nucleic acid product with a second restriction endonuclease that cleaves the second restriction endonuclease recognition sequence at each end of the first double-stranded nucleic acid product, (f) ligating ends of the first double-stranded nucleic acid product of step (e) to generate a second double-stranded circularized nucleic acid; and (g) amplifying the second double-stranded circularized nucleic acid using a third primer including a sequence that is substantially complementary to the first adapter and a fourth primer including a sequence that is substantially complementary to the second adapter, to generate a version of the double-stranded member of the nucleic acid library lacking all or a portion of the sequence encoding the constant region of the analyte.

Also provided herein are methods for removing all or a portion of a sequence encoding a constant region of an analyte from a double-stranded member of a nucleic acid library, where the double-stranded member of the nucleic acid library includes a first adaptor, a barcode, a capture domain, a sequence that is complementary to all or a portion of the sequence encoding the constant region of the analyte, and a second adaptor, wherein the method includes (a) adding to each end of the double-stranded member of the nucleic acid library a first restriction endonuclease recognition sequence, (b) contacting the double-stranded member of the nucleic acid library of step (a) with a first restriction endonuclease that cleaves the first restriction endonuclease recognition sequence at each end, (c) ligating ends of the double-stranded member of the nucleic acid library of step (b) to generate a first-double-stranded nucleic circularized nucleic acid, and (d) amplifying the double-stranded circularized nucleic acid using a first primer and a second primer to generate a version of the double-stranded member of the nucleic acid library lacking all, or a portion of, the sequence encoding the constant region of the analyte, wherein: the first primer includes (i) a sequence substantially complementary to a sequence from a 3' region of the sequence encoding the constant region of the analyte, and (ii) a sequence including a first functional domain; and the second primer includes (i) a sequence substantially complementary to a sequence from a 5' region of the sequence encoding the constant region of the analyte, and (ii) a sequence comprising a second functional domain.

In some embodiments of removing all or a portion of a sequence encoding a constant region of an analyte from a double-stranded member of a nucleic acid library, the double-stranded member of the nucleic acid library includes the first adaptor, the barcode, the capture domain, the sequence that is complementary to all or a portion of the sequence encoding the constant region of the analyte, and the second adaptor, in a 5' to a 3' direction. In some embodiments, the double-stranded member of the nucleic acid library includes a UMI disposed between the barcode and the capture domain. In some embodiments, the first primer includes (i) the sequence from the 3' region of the sequence encoding the constant region of the analyte and (ii) the second restriction endonuclease recognition sequence, in a 3' to a 5' direction. In some embodiments, the second primer includes (i) the sequence substantially complementary to the sequence from the 5' region of the sequence encoding the constant region of the analyte, and (ii) the second restriction endonuclease recognition sequence, in a 3' to a 5' direction. In some embodiments, ligating in step (c) and/or step (f) is performed using a ligase. In some embodiments, ligating in step (c) and/or step (f) is performed using template-mediated ligation (e.g., a splint oligonucleotide).

In some embodiments, the double-stranded member of a nucleic acid library includes a sequence that is complementary to all or a portion of a sequence encoding a variable region of the analyte. In some embodiments, the sequence that is complementary to all or a portion of the sequence encoding the constant region of the analyte is positioned 5' relative to the sequence that is complementary to all or a portion of the sequence encoding the variable region of the analyte. In some embodiments, the sequence that is complementary to all or a portion of the sequence encoding the constant region of the analyte is positioned 3' relative to the sequence that is complementary to all or a portion of the sequence encoding the variable region of the analyte.

In some embodiments, the method includes amplifying the double-stranded member of the nucleic acid library lacking all, or a portion of, the sequence encoding the constant region of the analyte using a third primer and fourth primer, where the third primer is substantially complementary to the first functional domain, and the fourth primer is substantially complementary to the second functional domain. In some embodiments, determining all, or a portion of, the sequence encoding the variable region of the analyte or complement thereof, and all or a portion of the sequence of the barcode or complement thereof. In some embodiments, determining the sequence comprises sequencing (i) all or a portion of the sequence encoding the variable region of the analyte or a complement thereof, and (ii) all or a portion of the sequence of the barcode or a complement thereof.

In some embodiments, the first primer includes a sequence substantially complementary to the reverse complement of the first adaptor, and a sequence including the first functional domain, in 3' to 5' direction. In some embodiments, the second primer includes a sequence substantially complementary to a sequence of the 5' region of the sequence encoding the constant region of the analyte, and a sequence including the second functional domain, in a 3' to 5' direction.

Also provided herein are methods for removing all or a portion of the sequence encoding a constant region of an analyte from a double-stranded member of a nucleic acid library, wherein the double-stranded member of the nucleic acid library includes a ligation sequence, a barcode, a reverse complement of a first adaptor, a capture domain, a sequence that is complementary to all or a portion of the sequence encoding the constant region of the analyte, and a second adaptor, wherein the method includes ligating ends of the double-stranded member using the ligation sequence as a splint (e.g., splint oligonucleotide) to and splint ligation, to generate a circularized double-stranded nucleic acid, amplifying the circularized double-stranded nucleic acid using a first primer and a second primer to generate a version of the double-stranded member of the nucleic acid library lacking all, or a portion of, the sequence encoding the constant region, wherein: the first primer includes (i) a sequence substantially complementary to the reverse complement of the first adaptor and (ii) a first functional domain and the second primer includes (i) a sequence substantially complementary to a sequence from a 5' region of the sequence encoding the constant region of the analyte, and (ii) a second functional domain.

In some embodiments, the double-stranded member of the nucleic acid library includes the ligation sequence, the barcode, the reverse complement of the first adaptor, the capture domain, the sequence complementary to all or a portion of the sequence encoding the constant region of the analyte, and the second adaptor, in a 5' to 3' direction. In some embodiments, the double-stranded member of the nucleic acid library includes a unique molecular identifier (UMI). In some embodiments, the UMI is disposed between the barcode and the reverse complement of the first adaptor.

In some embodiments, the first primer includes a sequence substantially complementary to the reverse complement of the first adaptor, and a sequence including the first functional domain, in 3' to 5' direction. In some embodiments, the second primer includes a sequence substantially complementary to a sequence of the 5' region of the sequence encoding the constant region of the analyte, and (ii) the sequence comprising the second functional domain, in a 3' to 5' direction.

In some embodiments, a third primer is substantially complementary to the first functional domain. In some embodiments, a fourth primer is substantially complementary to the second functional domain.

Also provided herein, are methods for removing all or a portion of a sequence encoding an analyte from a double-stranded member of a nucleic acid library, where the double-stranded member of the nucleic acid library includes a first adaptor, a barcode, a capture domain, a sequence that is complementary to all or a portion of the sequence encoding the analyte, and a second adaptor, where the method includes (a) adding to each end of the double-stranded member of the nucleic acid library a first restriction endonuclease recognition sequence, (b) contacting the double-stranded member of the nucleic acid library of step (a) with a first restriction endonuclease that cleaves the first restriction endonuclease recognition sequence at each end of the double-stranded member of the nucleic acid library, (c) ligating ends of the double-stranded member of the nucleic acid library of step (b) to generate a first double-stranded circularized nucleic acid, (d) amplifying the first double-stranded circularized nucleic acid using a first and a second primer to generate a first double-stranded nucleic acid product, where the first primer includes (i) a sequence substantially complementary to a 3' region of the sequence encoding the analyte and (ii) a second restriction endonuclease recognition sequence and the second primer includes (i) a sequence substantially complementary to a sequence from a 5' region of the sequence encoding the analyte, and (ii) the second restriction endonuclease recognition sequence, (e) contacting the first double-stranded nucleic acid product with a second restriction endonuclease that cleaves the second restriction endonuclease recognition sequence at each end of the first double-stranded nucleic acid product, (f) ligating ends of the first double-stranded nucleic acid product of step (e) to generate a second double-stranded circularized nucleic acid, and (g) amplifying the second double-stranded circularized nucleic acid using a third primer including a sequence that is substantially complementary to the first adapter and a fourth primer including a sequence that is substantially complementary to the second adapter, to generate a version of the double-stranded member of the nucleic acid library lacking all or a portion the sequence encoding the analyte.

Also provided herein are methods for removing all or a portion of a sequence encoding an analyte from a double-stranded member of a nucleic acid library, where the double-stranded member of the nucleic acid library includes a first adaptor, a barcode, a capture domain, a sequence that is complementary to all or a portion of the sequence encoding the analyte, and a second adaptor, where the method includes (a) adding to each end of the double-stranded member of the nucleic acid library a first restriction endonuclease recognition sequence, (b) contacting the double-stranded member of the nucleic acid library of step (a) with a first restriction endonuclease that cleaves the first restriction endonuclease recognition sequence at each end, (c) ligating ends of the double-stranded member of the nucleic acid library of step (b) to generate a first-double-stranded nucleic acid circularized nucleic acid, and (d) amplifying the double-stranded circularized nucleic acid using a first primer and a second primer to generate a version of the double-stranded member of the nucleic acid library lacking all, or a portion of, the sequence encoding the analyte, where the first primer includes (i) a sequence substantially complementary to a sequence from a 3' region of the sequence encoding the analyte, and (ii) a sequence including a first functional domain and the second primer includes (i) a sequence substantially complementary to a sequence from a 5' region of the sequence encoding the analyte, and (ii) a sequence including a second functional domain.

Also provided herein are methods for removing all or a portion of the sequence encoding an analyte from a double-stranded member of a nucleic acid library, where the double-stranded member of the nucleic acid library includes a ligation sequence, a barcode, a reverse complement of a first adaptor, a capture domain, a sequence that is complementary to all or a portion of the sequence encoding the analyte, and a second adaptor, where the method includes (a) ligating ends of the double-stranded member using the ligation sequence to splint ligation, to generate a circularized double-stranded nucleic acid, (b) amplifying the circularized double-stranded nucleic acid using a first primer and a second primer to generate a version of the double-stranded member of the nucleic acid library lacking all, or a portion of, the sequence encoding the analyte, where the first primer includes (i) a sequence substantially complementary to the reverse complement of the first adaptor and (ii) a first functional domain and the second primer includes (i) a sequence substantially complementary to a sequence from a 5' region of the sequence encoding the analyte, and (ii) a second functional domain. Also provided herein are methods of reversing the orientation of an analyte sequence of a double-stranded member of a nucleic acid library, wherein the double-stranded member of the nucleic acid library includes a ligation sequence, a barcode, a reverse complement of the first adaptor, an amplification domain, a capture domain, a sequence that is complementary to all or a portion of the sequence encoding the analyte, and a second adaptor, wherein the method includes (a) ligating ends of the double-stranded member of the nucleic acid library using the ligation sequence for splint ligation, to generate a circularized double-stranded nucleic acid and (b) amplifying the circularized double-stranded nucleic acid using a first primer and a second primer to generate a double-stranded nucleic acid product, where the first primer includes (i) a sequence substantially complementary to the reverse complement of the first adaptor and (ii) a functional domain; and the second primer includes a sequence substantially complementary to the amplification domain, thereby reversing the orientation of the analyte sequence of the double-stranded member of the nucleic acid library.

Some embodiments included herein describe removal of all or a portion of a constant region of an analyte, however, it will be appreciated by one of ordinary skill in the art that any portion of an analyte sequence can be removed by the methods described herein, such as for example, with a pair of primers designed to a 3' and a 5' portion of an analyte sequence (e.g., a captured analyte sequence, a complement of an analyte sequence, etc.).

In some embodiments, the double-stranded member of the nucleic acid library includes the ligation sequence, the barcode (e.g., a spatial barcode, a cell barcode), the reverse complement of the first adaptor, the amplification domain, the capture domain, the sequence complementary to all or a portion of the sequence encoding an analyte, and the second adaptor, in a 5' to 3' direction. In some embodiments, the double-stranded member of the nucleic acid library includes a unique molecular identifier (UMI). In some embodiments, the UMI is disposed between the barcode and the reverse complement of the first adaptor. In some embodiments, the first primer includes a sequence substantially complementary to the reverse complement of the first adaptor (e.g., Read 1), and a sequence comprising the first functional domain, in a 5' to 3' direction.

In some embodiments, the double-stranded member of the nucleic acid library includes a sequence that is complementary to all, or a portion of, a sequence encoding a 5' untranslated region of an analyte. In some embodiments, the double-stranded member of the nucleic acid library includes a complementary sequence to all, or a portion of, a sequence encoding a 3' untranslated region of an analyte. In some embodiments, a complementary sequence to all, or a portion of, the sequence encoding a 5' untranslated region of the analyte is positioned 5' relative to the sequence that is complementary to all, or a portion of, the sequence encoding the 3' untranslated region of the analyte. In some embodiments, the double-stranded member of the nucleic acid library includes one or more exons of the analyte. In some embodiments, the analyte includes a complementary sequence to all, or a portion of, the sequence encoding the 5' untranslated region of the analyte, the one or more exons, and the sequence that is complementary to all or a portion of the sequence encoding the 3' untranslated region, in a 5' to 3' direction.

In some embodiments of the nucleic acid preparation methods described herein, the double-stranded member of the nucleic acid library includes a complementary sequence to all, or a portion of, a sequence encoding a variable region of an analyte. In some embodiments, the sequence encoding the constant region of the analyte is positioned 5' relative to the sequence that is complementary to all or a portion of the sequence encoding the variable regions of the analyte. In some embodiments, the complementary sequence to all, or a portion of, the sequence encoding the constant region of the analyte is positioned 3' relative to the sequence that is complementary to all or a portion of the sequence encoding the variable region of the analyte.

Figure 6:
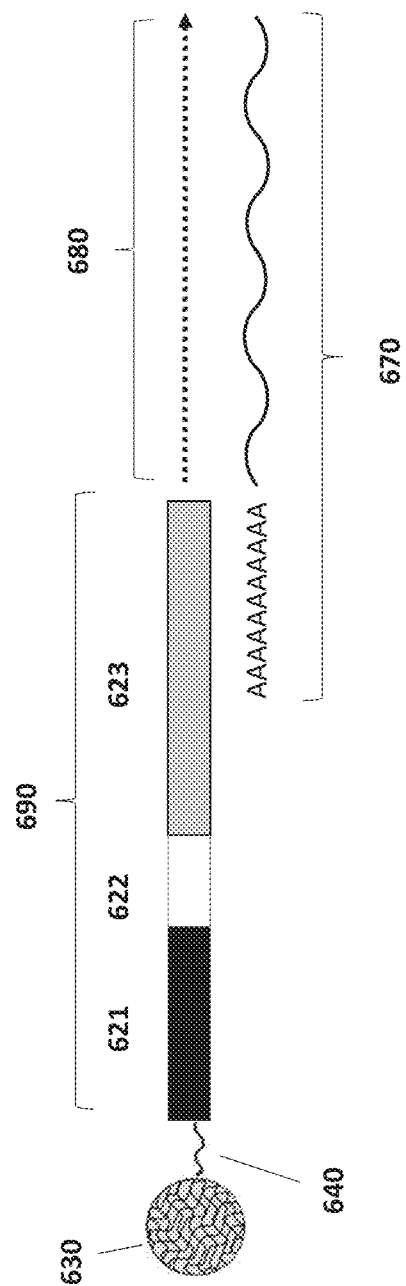
FIG. 6 shows an exemplary single-cell workflow.

In some embodiments, circularization of one or more analytes can be performed on single cells, including a general single cell capture configuration and workflow as generally depicted in FIG. 6. An exemplary method for capturing analytes from single cells and performing subsequent library preparation including circularization methods as described herein include a support 630 (e.g., a bead, such as a gel bead) comprising a nucleic acid barcode molecule 690 that are co-partitioned into a partition amongst a plurality of partitions (e.g., a droplet of a droplet emulsion or a well of a micro/nanowell array). In some embodiments, the partition comprises at most a single cell and a single support 630. In some embodiments, nucleic acid barcode molecule 690 is attached to support 630 via a releasable linkage 640 (e.g., comprising a labile bond). Upon release of nucleic acid barcode molecule 690 from the support 630, barcoded molecules may be generated within the partition. In some embodiments, nucleic acid barcode molecule 690 comprises sequence 623 complementary to a sequence of an RNA molecule 670 from a cell. In some instances, sequence 623 comprises a sequence specific for an RNA molecule. In some instances, sequence 623 comprises a poly-T sequence. In some instances, sequence 623 includes a sequence specific for an RNA molecule. In some instances, sequence 623 includes a sequence complementary to a region of an immune molecule, such as the constant region of a TCR or BCR sequence (as described herein). Sequence 623 is hybridized to RNA molecule 670 and a cDNA molecule 680 is generated in a reverse transcription reaction generating a barcoded nucleic acid molecule including cell (e.g., partition specific) barcode sequence 622 (or a reverse complement thereof) and a sequence of cDNA (or a portion thereof). Barcoded nucleic acid molecules can then be optionally processed as described elsewhere herein, e.g., to amplify the molecules and/or append sequencing platform specific sequences to the fragments. See, e.g., U.S. Pat. Pub. Nos. 20180105808 and 20190367969 and U.S. Pat. Nos. 10,273,541, 10,480,029, and 10,550,429, each of which is hereby incorporated by reference in its entirety. Barcoded nucleic acid molecules, or derivatives generated therefrom, can then be sequenced on a suitable sequencing platform. The methods described herein for circularization of a nucleic acid library is equally applicable for the libraries generated from a single cell workflow as previously described.

Analyte Sequences

The analyte sequences present in the nucleic acid library (e.g., nucleic acid library generated from single-cells or from a biological sample on an array) can be captured from a biological sample (e.g., any of the biological samples described herein). In some embodiments, the biological sample is a tissue sample. In some embodiments, the tissue sample is a tissue section. In some embodiments, the tissue section is a fixed tissue section. In some embodiments, the fixed tissue section is formalin-fixed paraffin-embedded tissue section. In some embodiments, the tissue section is a fresh, frozen tissue section.

Analyte sequences present in the nucleic acid library (e.g., a nucleic acid library generated from single-cells or from a biological sample on an array) can be obtained from RNA capture (e.g., any of the RNAs described herein). In some embodiments, the RNA is mRNA. In some embodiments, the analyte sequence present in the nucleic acid library are obtained from DNA. In some embodiments, the DNA is genomic DNA.

The captured analyte sequences in the nucleic acid library (e.g., nucleic acid library prepared from single-cells or an array) can be any analyte (e.g., mRNA) captured. For example, an analyte of interest can include a sequence of more than about 1 kb away from its 3' end and can be prepared by any of the methods described herein with analyte specific primers. In some embodiments, analyte sequences in the nucleic acid library include a constant region, such as a constant region present in an analyte encoding immune cell receptors. In some embodiments, analytes encoding immune cell receptors identify clonotypes or receptors from a biological sample, for example V(D)J sequences including CDR sequences (e.g., CDR 1, CDR 2, CDR 3).

In some embodiments, the analyte sequence of interest is for an immune cell receptor. In some embodiments, the immune cell receptor is a B cell receptor. In some embodiments, the B cell receptor is an immunoglobulin kappa light chain. In some embodiments, the variable region of the analyte includes a CDR3 of the immunoglobulin kappa light chain. In some embodiments, the variable region of the analyte includes one or both of CDR1 and CDR2 of the immunoglobulin kappa light chain. In some embodiments, the variable region of the analyte includes a full-length variable domain of the immunoglobulin kappa light chain.

In some embodiments, the B cell receptor is an immunoglobulin lambda light chain. In some embodiments, the variable region of the analyte includes a CDR3 of the immunoglobulin lambda light chain. In some embodiments, the variable region of the analyte includes one or both of CDR1 and CDR2 of the immunoglobulin lambda light chain. In some embodiments, the variable region of the analyte includes a full-length variable domain of the immunoglobulin lambda light chain.

In some embodiments, the B cell receptor is an immunoglobulin heavy chain. In some embodiments, the variable region of the analyte includes a CDR3 of the immunoglobulin heavy chain. In some embodiments, the variable region of the analyte includes one or both of CDR1 and CDR2 of the immunoglobulin heavy chain. In some embodiments, the variable region of the analyte includes a full-length variable domain of the immunoglobulin heavy chain.

In some embodiments, the immune cell receptor is a T cell receptor. In some embodiments, the T cell receptor is a T cell receptor alpha chain. In some embodiments, the variable region of the analyte includes a CDR3 of the T cell receptor alpha chain. In some embodiments, the variable region of the analyte includes one or both of CDR1 and CDR2 of the T cell receptor alpha chain. In some embodiments, the variable region of the analyte includes a full-length variable domain of the T cell receptor alpha chain.

In some embodiments, the T cell receptor is a T cell receptor beta chain. In some embodiments, the variable region of the analyte includes a CDR3 of the T cell receptor beta chain. In some embodiments, the variable region of the analyte includes one or both of CDR1 and CDR2 of the T cell receptor beta chain. In some embodiments, the variable region of the analyte further includes a full-length variable domain of the T cell receptor beta chain.

In some embodiments of the nucleic acid library preparation methods described herein, the methods include determining all or a portion of a sequence encoding the variable region of the analyte or a complement thereof, and all or a portion of the barcode or a complement thereof. In some embodiments, determining a sequence includes sequencing (e.g., any of the sequencing methods described herein) all, or a portion of, the sequence encoding the variable region of the analyte or a complement thereof, and all or a portion of the barcode or a complement thereof. In some embodiments, sequencing is performed using high-throughput sequencing. In some embodiments, sequencing is performed by sequencing-by-synthesis, sequencing-by-ligation, or sequencing-by-hybridization.

In some embodiments, the analyte is released from a biological sample. In some embodiments, a location of the analyte in the biological sample is determined using the sequences of a barcode. In some embodiments, the barcode is a spatial barcode. In some embodiments, an analyte is associated with a cell of a biological sample. In some embodiments, the analyte is associated with a cell of a biological sample by the sequence of a cell barcode.

In some embodiments of any of the spatial methods described herein, the method includes generating the double-stranded member of the nucleic acid library. In some embodiments, generating the double-stranded member of the nucleic acid library includes contacting the analyte with a capture probe comprising the first adaptor, the barcode (e.g., a spatial barcode, a cell barcode), and the capture domain, where the capture domain binds specifically to a sequence present in the analyte, extending an end of the capture probe using the analyte specifically bound to the capture domain as a template, thereby generating an extended capture probe, and adding the second adaptor to an end of the extended capture probe, thereby generating the double-stranded member of the nucleic acid library. In some embodiments, the capture probe includes the first adapter (e.g., Read 1), the barcode (e.g., a spatial barcode, a cell barcode), and the capture domain in a 5' to a 3' direction. In some embodiments, the capture probe is extended by a reverse transcriptase (e.g., any of the reverse transcriptases described herein). In some embodiments, a 3' end of the capture probe is extended to generate an extended capture probe. In some embodiments, the second adapter (e.g., a template switching oligonucleotide (TSO) sequence) is added to a 5' end of the extended capture probe.

Compositions

Provided herein are compositions including a double-stranded member of a nucleic acid library that includes a first adaptor, a barcode, a capture domain, a complementary analyte sequence including a sequence that is complementary to all or a portion of the sequence encoding the constant region of the analyte, and a second adaptor. In some embodiments, a unique molecular identifier is disposed between the barcode and the capture domain. In some embodiments, the barcode is a spatial barcode. In some compositions, the barcode is a cell barcode. In some compositions, the composition includes a first adaptor, a barcode, a UMI, a capture domain, a sequence complementary to all or a portion of the sequence encoding the constant region of the analyte, and a second adaptor in a 5' to 3' direction. In some compositions, the composition includes a double-stranded member of a nucleic acid library including a first restriction endonuclease recognition sequences added to each end of the double-stranded member of a nucleic acid library. In some compositions, the first restriction endonuclease recognition sequence is digested by a first restriction endonuclease thereby generating sticky ends on the double-stranded member of a nucleic acid library. In some compositions, the sticky ends of the double-stranded member of a nucleic acid library are ligated to each other intramolecularly to generate a first double-stranded circularized nucleic acid. In some compositions, the first double-stranded circularized nucleic acid is amplified with a first primer and second primer to generate a first double-stranded nucleic acid product (e.g., linearized), where a second restriction endonuclease recognition site is added to both ends of the first double-stranded nucleic acid product. In some compositions, the second restriction endonuclease recognition sequence (e.g., site) is digested by a second restriction endonuclease, thereby generating sticky ends on the first double-stranded nucleic acid product. In some compositions, the sticky ends of the first double-stranded nucleic acid product are ligated intramolecularly to generate a second double-stranded circularized nucleic acid. In some compositions, the second double-stranded circularized nucleic acid is amplified with a third primer and fourth primer to generate a version of the double-stranded member (e.g., linearized) of the nucleic acid library lacking all or a portion of the sequence encoding the constant region of the analyte.

In some compositions, after the step of generating the first double-stranded circularized nucleic acid, the first double-stranded circularized nucleic acid is amplified with a first primer and a second primer to generate a version of the nucleic acid product lacking all or a portion of the constant region of the analyte. In some compositions, the version of the nucleic acid product lacking all or a portion of the constant region of the analyte includes, in a 5' to 3' direction, a first functional domain, a portion of the constant region, a capture domain, a UMI, a barcode, a first adaptor, a second adaptor, the analyte sequence, and a second functional domain. In some compositions, the composition does not include any portion of the constant sequence.

Also provided herein are compositions including a double-stranded member of a nucleic acid library that includes a ligation sequence, barcode, a reverse complement of a first adaptor, a capture domain, a complementary analyte sequence including a sequence that is complementary to all or a portion of the sequence encoding the constant region of the analyte, and a second adaptor. In some compositions, a unique molecular identifier is disposed between the barcode and the reverse complement of a first adaptor. In some embodiments, the barcode is a spatial barcode. In some compositions, the barcode is a cell barcode. In some compositions, the composition includes a ligation sequence, a barcode, a UMI, a reverse complement to the first adaptor, a capture domain, a sequence complementary to all or a portion of the sequence encoding the constant region of the analyte, and a second adaptor in a 5' to 3' direction. In some compositions, the ends of the double-stranded member of the nucleic acid library are ligated intramolecularly to generate a circularized double-stranded nucleic acid product where the ligation sequence splints the ligation. In some compositions, the circularized double-stranded nucleic acid is amplified with a first primer and second primer to generate a version of the double-stranded member (e.g., linearized) of a nucleic acid library lacking all or a portion of the sequence encoding the constant region. In some compositions, the version of the double-stranded member of the nucleic acid library includes, in a 5' to 3' direction, a first functional domain (e.g., P5), a first adaptor, a unique molecular identifier, a barcode, a ligation sequence, a second adaptor, and a complementary analyte sequence.

Also provided herein are compositions including a double-stranded member of a nucleic acid library that includes a ligation sequence, barcode, a reverse complement of a first adaptor, an amplification domain, a capture domain, a complementary analyte sequence including a sequence that is complementary to all or a portion of the sequence encoding the constant region of the analyte, and a second adaptor. In some compositions, a unique molecular identifier is disposed between the barcode and the reverse complement of a first adaptor. In some embodiments, the barcode is a spatial barcode. In some compositions, the barcode is a cell barcode. In some compositions, the composition includes a ligation sequence, a barcode, a UMI, a reverse complement to the first adaptor, a capture domain, a sequence complementary to all or a portion of the sequence encoding the constant region of the analyte, and a second adaptor in a 5' to 3' direction. In some compositions, the ends of the double-stranded member of the nucleic acid library are ligated intramolecularly to generate a circularized double-stranded nucleic acid product where the ligation sequence splints the ligation. In some compositions, the circularized double-stranded nucleic acid is amplified with a first primer and second primer to generate a version of the double-stranded member (e.g., linearized) of a nucleic acid library lacking all or a portion of the sequence encoding the constant region. In some compositions the version of the double-stranded member of the nucleic acid library includes, in a 5' to 3' direction, a first functional domain (e.g., P5), a first adaptor, a unique molecular identifier, a barcode, a second adaptor, an analyte sequence where the orientation of the analyte sequence is reversed (e.g., the 5' end of the sequence is located 5' to the second adaptor), a capture domain, and an amplification domain.

Kits

Also provided herein are kits including (i) a first restriction endonuclease that cleaves a first restriction endonuclease recognition sequence; (ii) a second restriction endonuclease that cleaves a second restriction endonuclease recognition sequence; (iii) a ligase; and (iv) a first and a second primer, where: the first primer includes (i) a sequence from a 3' region of a sequence encoding a constant region of an analyte and (ii) the second restriction endonuclease recognition sequence and the second primer includes (i) a sequence substantially complementary to a sequence from a 5' region of the sequence encoding the constant region of the analyte, and (ii) the second restriction endonuclease recognition sequence. In some kits, the kit includes a third primer including a sequence that is substantially complementary to a first adapter and a fourth primer including a sequence that is substantially complementary to a second adapter. In some kits, the first primer includes (i) the sequence from the 3' region of the sequence encoding the constant region of the analyte and (ii) the second restriction endonuclease recognition sequence, in a 3' to a 5' direction. In some kits, the second primer includes (i) the sequence substantially complementary to the sequence from the 5' region of the sequence encoding the constant region of the analyte, and (ii) the second restriction endonuclease recognition sequence, in a 3' to a 5' direction. In some kits, the ligase is a DNA ligase. In some kits, the DNA ligase is T4 ligase.

Also provided herein are kits including (i) a first restriction endonuclease that cleaves a first restriction endonuclease recognition sequence, (ii) a ligase, and (iii) a first and a second primer, where the first primer includes: (i) a sequence from a 3' region of a sequence encoding a constant region of an analyte, and (ii) a sequence including a first functional domain, and the second primer includes (i) a sequence substantially complementary to a sequence from a 5' region of a sequence encoding the constant region of the analyte, and (ii) a sequence including a second functional domain. In some kits, the kit includes a third primer including a sequence substantially complementary to the first functional domain and a fourth primer including a sequence substantially complementary to the second functional domain. In some kits, the first primer includes (i) the sequence from the 3' region of sequence encoding a constant region of the analyte, and (ii) the sequence including the first functional domain, in a 3' to 5' direction. In some kits, the second primer includes (i) the sequence substantially complementary to the sequence from the 5' region of the sequence encoding the constant region of the analyte, and (ii) the sequence including the second functional domain, in a 3' to 5' direction. In some kits, the ligase is a DNA ligase. In some kits, the DNA ligase is T4 ligase.

Also provided herein are kits including (i) a first restriction endonuclease that cleaves a first restriction endonuclease recognition sequence, (ii) a ligase, and (iii) a first and a second primer, where the first primer includes (i) a sequence substantially complementary to a reverse complement of a first adaptor, and (ii) a sequence including a first functional domain; and the second primer includes (i) a sequence substantially complementary to a sequence from a 5' region of a sequence encoding the constant region of the analyte, and (ii) a sequence including a second functional domain. In some kits, the kit includes a third primer including a sequence substantially complementary to the first functional domain and a fourth primer including a sequence substantially complementary to the second functional domain. In some kits, the first primer includes (i) the sequence substantially complementary to the reverse complement of the first adaptor, and (ii) the sequence including the first functional domain, in a 3' to 5' direction. In some kits, the second primer includes (i) the sequence substantially complementary to the sequence from the 5' region of the sequence encoding the constant region of the analyte, and (ii) the sequence including the second functional domain, in a 3' to 5' direction. In some kits, the ligase is a DNA ligase. In some kits, the DNA ligase is T4 ligase.

Also provided herein are kits including (i) a first restriction endonuclease that cleaves a first restriction endonuclease recognition sequence, (ii) a ligase, and (iii) a first and a second primer, where the first primer includes (i) a sequence substantially complementary to a reverse complement of a first adaptor, and (ii) a functional domain; and the second primer includes a sequence substantially complementary to the amplification domain. In some kits, the kit includes a third primer including a sequence substantially complementary to the functional domain, and a fourth primer including a sequence substantially complementary to a reverse complement of the amplification domain. In some kits, the first primer includes (i) the sequence substantially complementary to the reverse complement of the first adaptor, and (ii) the sequence including the functional domain, in a 3' to 5' direction. In some kits, the ligase is a DNA ligase. In some kits, the DNA ligase is T4 ligase.

EMBODIMENTS

Embodiment 1 is a method for removing all or a portion of a sequence encoding a constant region of an analyte from a double-stranded member of a nucleic acid library, wherein the double-stranded member of the nucleic acid library comprises: a first adaptor, a barcode, a capture domain, a sequence that is complementary to all or a portion of the sequence encoding the constant region of the analyte, and a second adaptor, wherein the method comprises: (a) adding to each end of the double-stranded member of the nucleic acid library a first restriction endonuclease recognition sequence; (b) contacting the double-stranded member of the nucleic acid library of step (a) with a first restriction endonuclease that cleaves the first restriction endonuclease recognition sequence at each end of the double-stranded member of the nucleic acid library; (c) ligating ends of the double-stranded member of the nucleic acid library of step (b) to generate a first double-stranded circularized nucleic acid; (d) amplifying the first double-stranded circularized nucleic acid using a first and a second primer to generate a first double-stranded nucleic acid product, wherein: the first primer comprises: (i) a sequence substantially complementary to a 3' region of the sequence encoding the constant region of the analyte and (ii) a second restriction endonuclease recognition sequence; and the second primer comprises: (i) a sequence substantially complementary to a sequence from a 5' region of the sequence encoding the constant region of the analyte, and (ii) the second restriction endonuclease recognition sequence; (e) contacting the first double-stranded nucleic acid product with a second restriction endonuclease that cleaves the second restriction endonuclease recognition sequence at each end of the first double-stranded nucleic acid product; (f) ligating ends of the first double-stranded nucleic acid product of step (e) to generate a second double-stranded circularized nucleic acid; and (g) amplifying the second double-stranded circularized nucleic acid using a third primer comprising a sequence that is substantially complementary to the first adapter and a fourth primer comprising a sequence that is substantially complementary to the second adapter, to generate a version of the double-stranded member of the nucleic acid library lacking all or a portion of the sequence encoding the constant region of the analyte.

Embodiment 2 is the method of embodiment 1, wherein the double-stranded member of the nucleic acid library comprises the first adaptor, the barcode, the capture domain, the sequence that is complementary to all or a portion of the sequence encoding the constant region of the analyte, and the second adaptor, in a 5' to 3' direction.

Embodiment 3 is the method of embodiment 2, wherein the double-stranded member of the nucleic acid library further comprises a UMI disposed between the barcode and the capture domain.

Embodiment 4 is the method of any one of embodiments 1-3, wherein the first primer comprises (i) the sequence from the 3' region of the sequence encoding the constant region of the analyte and (ii) the second restriction endonuclease recognition sequence, in a 3' to a 5' direction.

Embodiment 5 is the method of any one of embodiments 1-4, wherein the second primer comprises (i) the sequence substantially complementary to the sequence from the 5' region of the sequence encoding the constant region of the analyte, and (ii) the second restriction endonuclease recognition sequence, in a 3' to 5' direction.

Embodiment 6 is the method of any one of embodiments 1-5, wherein the ligating in step (c) and/or step (f) is performed using a ligase or using template mediated ligation.

Embodiment 7 is the method of embodiment 6, wherein the ligase is a DNA ligase.

Embodiment 8 is the method of embodiment 7, wherein the DNA ligase is a T4 ligase.

Embodiment 9 is the method of any one of embodiments 1-8, wherein the barcode is a cell barcode or a spatial barcode.

Embodiment 10 is the method of any one of embodiments 1-9, wherein the nucleic acid library is a DNA library.

Embodiment 11 is the method of any one of embodiments 1-10, wherein the nucleic acid library is a cDNA library.

Embodiment 12 is the method of any one of embodiments 1-11, wherein the double-stranded member of a nucleic acid library further comprises a sequence that is complementary to all or a portion of a sequence encoding a variable region of the analyte.

Embodiment 13 is the method of embodiment 12, wherein the sequence that is complementary to all or a portion of the sequence encoding the constant region of the analyte is positioned 5' relative to the sequence that is complementary to all or a portion of the sequence encoding the variable region of the analyte.

Embodiment 14 is the method of embodiment 12, wherein the sequence that is complementary to all or a portion of the sequence encoding the constant region of the analyte is positioned 3' relative to the sequence that is complementary to all or a portion of the sequence encoding the variable region of the analyte.

Embodiment 15 is the method of any one of embodiments 12-14, wherein the analyte is an immune cell receptor.

Embodiment 16 is the method of embodiment 15, wherein the immune cell receptor is a B cell receptor.

Embodiment 17 is the method of embodiment 16, wherein the B cell receptor is an immunoglobulin kappa light chain.

Embodiment 18 is the method of embodiment 17, wherein the variable region of the analyte comprises a CDR3 of the immunoglobulin kappa light chain.

Embodiment 19 is the method of embodiment 18, wherein the variable region of the analyte further comprises one or both of CDR1 and CDR2 of the immunoglobulin kappa light chain.

Embodiment 20 is the method of embodiment 18, wherein the variable region of the analyte further comprises a full-length variable domain of the immunoglobulin kappa light chain.

Embodiment 21. The method of embodiment 16, wherein the B cell receptor is an immunoglobulin lambda light chain.

Embodiment 22 is the method of embodiment 21, wherein the variable region of the analyte comprises a CDR3 of the immunoglobulin lambda light chain.

Embodiment 23 is the method of embodiment 22, wherein the variable region of the analyte further comprises one or both of CDR1 and CDR2 of the immunoglobulin lambda light chain.

Embodiment 24 is the method of embodiment 22, wherein the variable region of the analyte further comprises a full-length variable domain of the immunoglobulin lambda light chain.

Embodiment 25 is the method of embodiment 16, wherein the B cell receptor is an immunoglobulin heavy chain.

Embodiment 26 is the method of embodiment 25, wherein the variable region of the analyte comprises a CDR3 of the immunoglobulin heavy chain.

Embodiment 27 is the method of embodiment 26, wherein the variable region of the analyte further comprises one or both of CDR1 and CDR2 of the immunoglobulin heavy chain.

Embodiment 28 is the method of embodiment 26, wherein the variable region of the analyte further comprises a full-length variable domain of the immunoglobulin heavy chain.

Embodiment 29 is the method of embodiment 15, wherein the immune cell receptor is a T cell receptor.

Embodiment 30 is the method of embodiment 29, wherein the T cell receptor is a T cell receptor alpha chain.

Embodiment 31 is the method of embodiment 30, wherein the variable region of the analyte comprises a CDR3 of the T cell receptor alpha chain.

Embodiment 32 is the method of embodiment 31, wherein the variable region of the analyte further comprises one or both of CDR1 and CDR2 of the T cell receptor alpha chain.

Embodiment 33 is the method of embodiment 31, wherein the variable region of the analyte further comprises a full-length variable domain of the T cell receptor alpha chain.

Embodiment 34 is the method of embodiment 29, wherein the T cell receptor is a T cell receptor beta chain.

Embodiment 35 is the method of embodiment 34, wherein the variable region of the analyte comprises a CDR3 of the T cell receptor beta chain.

Embodiment 36 is the method of embodiment 35, wherein the variable region of the analyte further comprises one or both of CDR1 and CDR2 of the T cell receptor beta chain.

Embodiment 37 is the method of embodiment 35, wherein the variable region of the analyte further comprises a full-length variable domain of the T cell receptor beta chain.

Embodiment 38 is the method of any one of embodiments 12-37, wherein the method further comprises: (h) determining (i) all or a portion of a sequence encoding the variable region of the analyte or a complement thereof, and (ii) all or a portion of the barcode or a complement thereof.

Embodiment 39 is the method of embodiment 38, wherein the determining in step (h) comprises sequencing (i) all or a portion of the sequence encoding the variable region of the analyte or a complement thereof, and (ii) all or a portion of the barcode or a complement thereof.

Embodiment 40 is the method of embodiment 38 or 39, wherein the analyte was released from a biological sample, and the method further comprises: determining a location of the analyte in the biological sample using the determined sequences of (i) and (ii).

Embodiment 41 is the method of any one of embodiments 1-40, further comprising generating the double-stranded member of the nucleic acid library.

Embodiment 42 is the method of embodiment 41, wherein the step of generating the double-stranded member of the nucleic acid library comprises: contacting the analyte with a capture probe comprising the first adaptor, the barcode, and the capture domain, wherein the capture domain binds specifically to a sequence present in the analyte; extending an end of the capture probe using the analyte specifically bound to the capture domain as a template, thereby generating an extended capture probe; and adding the second adaptor an end of the extended capture probe, thereby generating the double-stranded member of the nucleic acid library.

Embodiment 43 is the method of embodiment 42, wherein the capture probe comprises the first adapter, the barcode, and the capture domain in a 5' to a 3' direction.

Embodiment 44 is the method of embodiment 42 or 43, wherein a 3' end of the capture probe is extended.

Embodiment 45 is the method of any one of embodiments 42-44, wherein the second adapter is added to a 5' end of the extended capture probe.

Embodiment 46 is the method of any one of embodiments 1-45, wherein the biological sample is a tissue sample, a tissue section or a fixed tissue section.

Embodiment 47 is the method of embodiment 46, wherein the fixed tissue section is formalin-fixed paraffin-embedded tissue section or the tissue section is a fresh, frozen tissue section.

Embodiment 48 is the method of any one of embodiments 1-47, wherein the analyte is an RNA.

Embodiment 49 is the method of embodiment 48, wherein the RNA is an mRNA.

Embodiment 50 is the method of any one of embodiments 1-47, wherein the analyte is a DNA.

Embodiment 51 is the method of embodiment 50, wherein the DNA is genomic DNA.

Embodiment 52 is a kit comprising: (i) a first restriction endonuclease that cleaves a first restriction endonuclease recognition sequence; (ii) a second restriction endonuclease that cleaves a second restriction endonuclease recognition sequence; (iii) a ligase; and (iv) a first and a second primer, wherein: the first primer comprises: (i) a sequence from a 3' region of a sequence encoding a constant region of an analyte and (ii) the second restriction endonuclease recognition sequence; and the second primer comprises: (i) a sequence substantially complementary to a sequence from a 5' region of the sequence encoding the constant region of the analyte, and (ii) the second restriction endonuclease recognition sequence.

Embodiment 53 is the kit of embodiment 53, wherein the kit further comprises: a third primer comprising a sequence that is substantially complementary to a first adapter; and a fourth primer comprising a sequence that is substantially complementary to a second adapter.

Embodiment 54 is the kit of embodiment 52 or 53, wherein the first primer comprises (i) the sequence from the 3' region of the sequence encoding the constant region of the analyte and (ii) the second restriction endonuclease recognition sequence, in a 3' to a 5' direction.

Embodiment 55 is the kit of any one of embodiments 52-54, wherein the second primer comprises (i) the sequence substantially complementary to the sequence from the 5' region of the sequence encoding the constant region of the analyte, and (ii) the second restriction endonuclease recognition sequence, in a 3' to a 5' direction.

Embodiment 56 is the kit of any one of embodiments 52-55, wherein the ligase is a DNA ligase.

Embodiment 57 is the kit of embodiment 56, wherein the DNA ligase is T4 ligase.

Embodiment 58 is a method for removing all or a portion of a sequence encoding a constant region of an analyte from a double-stranded member of a nucleic acid library, wherein the double-stranded member of the nucleic acid library comprises: a first adaptor, a barcode, a capture domain, a sequence that is complementary to all or a portion of the sequence encoding the constant region of the analyte, and a second adaptor, wherein the method comprises:
(a) adding to each end of the double-stranded member of the nucleic acid library a first restriction endonuclease recognition sequence; (b) contacting the double-stranded member of the nucleic acid library of step (a) with a first restriction endonuclease that cleaves the first restriction endonuclease recognition sequence at each end; (c) ligating ends of the double-stranded member of the nucleic acid library of step (b) to generate a first-double-stranded nucleic acid circularized nucleic acid; and (d) amplifying the double-stranded circularized nucleic acid using a first primer and a second primer to generate a version of the double-stranded member of the nucleic acid library lacking all, or a portion of, the sequence encoding the constant region of the analyte, wherein: the first primer comprises: (i) a sequence substantially complementary to a sequence from a 3' region of the sequence encoding the constant region of the analyte, and (ii) a sequence comprising a first functional domain; and the second primer comprises: (i) a sequence substantially complementary to a sequence from a 5' region of the sequence encoding the constant region of the analyte, and (ii) a sequence comprising a second functional domain.

Embodiment 59 is the method of embodiment 58, wherein the double-stranded member of the nucleic acid library comprises the first adaptor, the barcode, the capture domain, the sequence complementary to all or a portion of the sequence encoding the constant region of the analyte, and the second adaptor, in a 5' to 3' direction.

Embodiment 60 is the method of embodiment 58 or 59, wherein the double-stranded member of the nucleic acid library further comprises a unique molecular identifier (UMI) disposed between the spatial barcode and the capture domain.

Embodiment 61 is the method of any one of embodiments 58-60, wherein the first primer comprises (i) the sequence from the 3' region of the sequence encoding the constant region of the analyte, and (ii) the sequence comprising the first functional domain, in 3' to 5' direction; and wherein the second primer comprises (i) the sequence from the 5' region of the sequence encoding the constant region of the analyte, and (ii) the sequence comprising the second functional domain, in a 3' to 5' direction.

Embodiment 62 is the method of any one of embodiments 58-61, wherein the barcode is a spatial barcode or a cell barcode.

Embodiment 63 is the method of any one of embodiments 58-62, wherein ligating in step (c) is performed using a DNA ligase or using template mediated ligation.

Embodiment 64 is the method of embodiment 63, wherein the DNA ligase is T4 ligase.

Embodiment 65 is the method of any one of embodiments 58-64, wherein the nucleic acid library is a DNA library.

Embodiment 66 is the method of any one of embodiments 58-64, wherein the nucleic acid library is a cDNA library.

Embodiment 67 is the method of any one of embodiments 58-66, wherein the double-stranded member of the nucleic acid library further comprises a sequence that is complementary to all or a portion of a sequence encoding a variable region of an analyte.

Embodiment 68 is the method of embodiment 67, wherein the sequence complementary to all or a portion of the sequence encoding the constant region of the analyte is positioned 5' relative to the sequence that is complementary to all or a portion of the sequence encoding the variable regions of the analyte.

Embodiment 69 is the method of embodiment 67, wherein the sequence complementary to all or a portion of the sequence encoding the constant region of the analyte is positioned 3' relative to the sequence that is complementary to all or a portion of the sequence encoding the variable region of the analyte.

Embodiment 70 is the method of any one of embodiments 67-69, wherein the analyte is an immune cell receptor.

Embodiment 71 is the method of embodiment 70, wherein the immune cell receptor is a B cell receptor.

Embodiment 72 is the method of embodiment 71, wherein the B cell receptor is an immunoglobulin kappa light chain.

Embodiment 73 is the method of embodiment 72, wherein the variable region of the analyte comprises a CDR3 of the immunoglobulin kappa light chain.

Embodiment 74 is the method of embodiment 73, wherein the variable region of the analyte further comprises one or both of CDR1 and CDR2 of the immunoglobulin kappa light chain.

Embodiment 75 is the method of embodiment 73, wherein the variable region of the analyte further comprises a full-length variable domain of the immunoglobulin kappa light chain.

Embodiment 76 is the method of embodiment 71, wherein the B cell receptor is an immunoglobulin lambda light chain.

Embodiment 77 is the method of embodiment 76, wherein the variable region of the analyte comprises a CDR3 of the immunoglobulin kappa light chain.

Embodiment 78 is the method of embodiment 77, wherein the variable region of the analyte further comprises one or both of CDR1 and CDR2 of the immunoglobulin kappa light chain.

Embodiment 79 is the method of embodiment 77, wherein the variable region of the analyte further comprises a full-length variable domain of the immunoglobulin lambda light chain.

Embodiment 80 is the method of embodiment 71, wherein the B cell receptor is an immunoglobulin heavy chain.

Embodiment 81 is the method of embodiment 80, wherein the variable region of the analyte comprises a CDR3 of the immunoglobulin heavy chain.

Embodiment 82 is the method of embodiment 81, wherein the variable region of the analyte further comprises one or both of CDR1 and CDR2 of the immunoglobulin heavy chain.

Embodiment 83 is the method of embodiment 81, wherein the variable region of the analyte further comprises a full-length variable domain of the immunoglobulin heavy chain.

Embodiment 84 is the method of embodiment 70, wherein the immune cell receptor is a T cell receptor.

Embodiment 85 is the method of embodiment 84, wherein the T cell receptor is a T cell receptor alpha chain.

Embodiment 86 is the method of embodiment 85, wherein the variable region of the analyte comprises a CDR3 of the T cell receptor alpha chain.

Embodiment 87 is the method of embodiment 86, wherein the variable region of the analyte further comprises one or both of CDR1 and CDR2 of the T cell receptor alpha chain.

Embodiment 88 is the method of embodiment 86, wherein the variable region of the analyte further comprises a full-length variable domain of the T cell receptor alpha chain.

Embodiment 89 is the method of embodiment 84, wherein the T cell receptor is a T cell receptor beta chain.

Embodiment 90 is the method of embodiment 89, wherein the variable region of the analyte comprises a CDR3 of the T cell receptor beta chain.

Embodiment 91 is the method of embodiment 90, wherein the variable region of the analyte further comprises one or both of CDR1 and CDR2 of the T cell receptor beta chain.

Embodiment 92 is the method of embodiment 90, wherein the variable region of the analyte further comprises a full-length variable domain of the T cell receptor beta chain.

Embodiment 93 is the method of any one of embodiments 58-92, wherein the method further comprises amplifying the version of the double-stranded member of the nucleic acid library lacking all, or a portion of, the sequence encoding the constant region of the analyte using a third primer and fourth primer, wherein: the third primer is substantially complementary to the first functional domain, and the fourth primer is substantially complementary to the second functional domain.

Embodiment 94 is the method of any one of embodiments 58-93, wherein the method further comprises: determining (i) all or a portion of the sequence encoding the variable region of the analyte or complement thereof, and (ii) all or a portion of the sequence of the barcode or complement thereof.

Embodiment 95 is the method of embodiment 94, wherein determining the sequence comprises sequencing (i) all or a portion of the sequence encoding the variable region of the analyte or a complement thereof, and (ii) all or a portion of the sequence of the barcode or a complement thereof.

Embodiment 96 is the method of embodiment 95, wherein the sequencing is performed by sequence by synthesis, sequence by ligation or sequence by hybridization.

Embodiment 97 is the method of any one of embodiments 94-103, wherein the analyte was released from a biological sample, and the method further comprises: determining the location of the analyte in the biological sample using the determined sequence of (i) and (ii).

Embodiment 98 is the method of any one of embodiments 58-97, further comprising generating the double-stranded member of the nucleic acid library.

Embodiment 99 is the method of embodiment 98, wherein the step of generating the double-stranded member of the nucleic acid library comprises: contacting the analyte with a capture probe comprising the first adaptor, the barcode, and the capture domain, wherein the capture domain binds specifically to a sequence present in the analyte; extending an end of the capture probe using the analyte specifically bound to the capture domain as a template, thereby generating an extended capture probe; and adding the second adaptor to an end of the extended capture probe, thereby generating the double-stranded member of the nucleic acid library.

Embodiment 100 is the method of embodiment 99, wherein the capture probe comprises the first adapter, the barcode, and the capture domain in a 5' to a 3' direction.

Embodiment 101 is the method of embodiment 99 or 100, wherein a 3' end of the capture probe is extended.

Embodiment 102 is the method of any one of embodiments 100-101, wherein the second adapter is added to a 5' end of the extended capture probe.

Embodiment 103 is the method of any one of embodiments 58-102, wherein the biological sample is a tissue sample, a tissue section or a fixed tissue section.

Embodiment 104 is the method of embodiment 103, wherein the fixed tissue section is formalin-fixed paraffin-embedded tissue section or a fresh, frozen tissue section.

Embodiment 105 is the method of any one of embodiments 58-104, wherein the analyte is an RNA.

Embodiment 106 is the method of embodiment 105, wherein the RNA is an mRNA.

Embodiment 107 is the method of any one of embodiments 58-104, wherein the analyte is a DNA.

Embodiment 108 is the method of embodiment 107, wherein the DNA is genomic DNA.

Embodiment 109 is a kit comprising: (i) a first restriction endonuclease that cleaves a first restriction endonuclease recognition sequence; (ii) a ligase; and (iii) a first and a second primer, wherein: the first primer comprises: (i) a sequence from a 3' region of a sequence encoding a constant region of an analyte, and (ii) a sequence comprising a first functional domain; and the second primer comprises: (i) a sequence substantially complementary to a sequence from a 5' region of a sequence encoding the constant region of the analyte, and (ii) a sequence comprising a second functional domain.

Embodiment 110 is the kit of embodiment 109, wherein the kit further comprises: a third primer comprising a sequence substantially complementary to the first functional domain; and a fourth primer comprising a sequence substantially complementary to the second functional domain.

Embodiment 111 is the kit of embodiment 108 or 109, wherein the first primer comprises (i) the sequence from the 3' region of sequence encoding a constant region of the analyte, and (ii) the sequence comprising the first functional domain, in a 3' to 5' direction.

Embodiment 112 is the kit of any one of embodiments 108-111, wherein the second primer comprises (i) the sequence substantially complementary to the sequence from the 5' region of the sequence encoding the constant region of the analyte, and (ii) the sequence comprising the second functional domain, in a 3' to 5' direction.

Embodiment 113 is the kit of any one of embodiments 108-112, wherein the ligase is a DNA ligase.

Embodiment 114 is the kit of embodiment 113, wherein the DNA ligase is T4 ligase.

Embodiment 115 is a method for removing all or a portion of the sequence encoding a constant region of an analyte from a double-stranded member of a nucleic acid library, wherein the double-stranded member of the nucleic acid library comprises a ligation sequence, a barcode, a reverse complement of a first adaptor, a capture domain, a sequence that is complementary to all or a portion of the sequence encoding the constant region of the analyte, and a second adaptor, wherein the method comprises: (a) ligating ends of the double-stranded member using the ligation sequence to splint ligation, to generate a circularized double-stranded nucleic acid; (b) amplifying the circularized double-stranded nucleic acid using a first primer and a second primer to generate a version of the double-stranded member of the nucleic acid library lacking all, or a portion of, the sequence encoding the constant region, wherein: the first primer comprises: (i) a sequence substantially complementary to the reverse complement of the first adaptor and (ii) a first functional domain; and the second primer comprises: (i) a sequence substantially complementary to a sequence from a 5' region of the sequence encoding the constant region of the analyte, and (ii) a second functional domain.

Embodiment 116 is the method of embodiment 115, wherein the double-stranded member of the nucleic acid library comprises the ligation sequence, the barcode, the reverse complement of the first adaptor, the capture domain, the sequence complementary to all or a portion of the sequence encoding the constant region of the analyte, and the second adaptor, in a 5' to 3' direction.

Embodiment 117 is the method of embodiment 116, wherein the double-stranded member of the nucleic acid library further comprises a unique molecular identifier (UMI) disposed between the barcode and the reverse complement of the first adaptor.

Embodiment 118 is the method of any one of embodiments 115-118, wherein the first primer comprises (i) the sequence substantially complementary to the reverse complement of the first adaptor, and (ii) the sequence comprising the first functional domain, in 3' to 5' direction; and wherein the second primer comprises (i) the sequence substantially complementary to a sequence of the 5' region of the sequence encoding the constant region of the analyte, and (ii) the sequence comprising the second functional domain, in a 3' to 5' direction.

Embodiment 119 is the method of any one of embodiments 115-118, wherein ligating in step (a) is performed using a DNA ligase.

Embodiment 120 is the method of embodiment 119, wherein the DNA ligase is T4 ligase.

Embodiment 121 is the method of any one of embodiments 115-120, wherein the barcode is a spatial barcode or a cell barcode.

Embodiment 122 is the method of any one of embodiments 115-121, wherein the nucleic acid library is a DNA library.

Embodiment 123 is the method of any one of embodiments 121-121, wherein the nucleic acid library is a cDNA library.

Embodiment 124 is the method of any one of embodiments 115-123, wherein the double-stranded member of the nucleic acid library further comprises a sequence that is complementary to all or a portion of a sequence encoding a variable region of an analyte.

Embodiment 125 is the method of embodiment 124, wherein the sequence complementary to all or a portion of the sequence encoding the constant region of the analyte is positioned 5' relative to the sequence that is complementary to all or a portion of the sequence encoding the variable regions of the analyte.

Embodiment 126 is the method of embodiment 124, wherein the sequence complementary to all or a portion of the sequence encoding the constant region of the analyte is positioned 3' relative to the sequence that is complementary to all or a portion of the sequence encoding the variable region of the analyte.

Embodiment 127 is the method of any one of embodiments 124-126, wherein the analyte is an immune cell receptor.

Embodiment 128 is the method of embodiment 127, wherein the immune cell receptor is a B cell receptor.

Embodiment 129 is the method of embodiment 128, wherein the B cell receptor is an immunoglobulin kappa light chain.

Embodiment 130 is the method of embodiment 129, wherein the variable region of the analyte comprises a CDR3 of the immunoglobulin kappa light chain.

Embodiment 131 is the method of embodiment 130, wherein the variable region of the analyte further comprises one or both of CDR1 and CDR2 of the immunoglobulin kappa light chain.

Embodiment 132 is the method of embodiment 130, wherein the variable region of the analyte further comprises a full-length variable domain of the immunoglobulin kappa light chain.

Embodiment 133 is the method of embodiment 128, wherein the B cell receptor is an immunoglobulin lambda light chain.

Embodiment 134 is the method of embodiment 133, wherein the variable region of the analyte comprises a CDR3 of the immunoglobulin kappa light chain.

Embodiment 135 is the method of embodiment 134, wherein the variable region of the analyte further comprises one or both of CDR1 and CDR2 of the immunoglobulin kappa light chain.

Embodiment 136 is the method of embodiment 134, wherein the variable region of the analyte further comprises a full-length variable domain of the immunoglobulin lambda light chain.

Embodiment 137 is the method of embodiment 128, wherein the B cell receptor is an immunoglobulin heavy chain.

Embodiment 138 is the method of embodiment 137, wherein the variable region of the analyte comprises a CDR3 of the immunoglobulin heavy chain.

Embodiment 139 is the method of embodiment 138, wherein the variable region of the analyte further comprises one or both of CDR1 and CDR2 of the immunoglobulin heavy chain.

Embodiment 140 is the method of embodiment 138, wherein the variable region of the analyte further comprises a full-length variable domain of the immunoglobulin heavy chain.

Embodiment 141 is the method of embodiment 127, wherein the immune cell receptor is a T cell receptor.

Embodiment 142 is the method of embodiment 141, wherein the T cell receptor is a T cell receptor alpha chain.

Embodiment 143 is the method of embodiment 142, wherein the variable region of the analyte comprises a CDR3 of the T cell receptor alpha chain.

Embodiment 144 is the method of embodiment 143, wherein the variable region of the analyte further comprises one or both of CDR1 and CDR2 of the T cell receptor alpha chain.

Embodiment 145 is the method of embodiment 143, wherein the variable region of the analyte further comprises a full-length variable domain of the T cell receptor alpha chain.

Embodiment 146 is the method of embodiment 141, wherein the T cell receptor is a T cell receptor beta chain.

Embodiment 147 is the method of embodiment 146, wherein the variable region of the analyte comprises a CDR3 of the T cell receptor beta chain.

Embodiment 148 is the method of embodiment 147, wherein the variable region of the analyte further comprises one or both of CDR1 and CDR2 of the T cell receptor beta chain.

Embodiment 149 is the method of embodiment 147, wherein the variable region of the analyte further comprises a full-length variable domain of the T cell receptor beta chain.

Embodiment 150 is the method of any one of embodiments 115-149, wherein the method further comprises amplifying the version of the double-stranded member of the nucleic acid library lacking all, or a portion of, the sequence encoding the constant region of the analyte using a third primer and fourth primer, wherein: the third primer is substantially complementary to the first functional domain, and the fourth primer is substantially complementary to the second functional domain.

Embodiment 151 is the method of any one of embodiments 115-150, wherein the method further comprises: determining (i) all or a portion of the sequence encoding the variable region of the analyte or complement thereof, and (ii) all or a portion of the sequence of the barcode or complement thereof.

Embodiment 152 is the method of embodiment 151, wherein the determining the sequence comprises sequencing (i) all or a portion of the sequence encoding the variable region of the analyte or a complement thereof, and (ii) all or a portion of the sequence of the barcode or a complement thereof.

Embodiment 153 is the method of embodiment 152, wherein the sequencing is performed using sequence by synthesis, sequence by ligation or sequence by hybridization.

Embodiment 154 is the method of any one of embodiments 151-153, wherein the analyte was released from a biological sample, and the method further comprises: determining the location of the analyte in the biological sample using the determined sequence of (i) and (ii).

Embodiment 155 is the method of any one of embodiments 115-154, further comprising generating the double-stranded member of the nucleic acid library.

Embodiment 156 is the method of embodiment 155, wherein the step of generating the double-stranded member of the nucleic acid library comprises: contacting the analyte with a capture probe comprising the ligation sequence, the barcode, the reverse complement of the first adaptor, the capture domain a sequence that is complementary to all or a portion of the sequence encoding the constant region of the analyte, and a second adaptor, wherein the capture domain binds specifically to a sequence present in the analyte; extending an end of the capture probe using the analyte specifically bound to the capture domain as a template, thereby generating an extended capture probe; and adding the second adaptor to an end of the extended capture probe, thereby generating the double-stranded member of the nucleic acid library.

Embodiment 157 is the method of embodiment 156, wherein the capture probe comprises the ligation sequence, the barcode, the reverse complement of the first adaptor, and the capture domain in a 5' to a 3' direction.

Embodiment 158 is the method of embodiment 156 or 157, wherein a 3' end of the capture probe is extended.

Embodiment 159 is the method of any one of embodiments 156-158, wherein the second adapter is added to a 5' end of the extended capture probe.

Embodiment 160 is the method of any one of embodiments 115-159, wherein the biological sample is a tissue sample, a tissue section, or a fixed tissue section.

Embodiment 161 is the method of embodiment 160, wherein the fixed tissue section is formalin-fixed paraffin-embedded tissue section or the tissue section is a fresh, frozen tissue section.

Embodiment 162 is the method of any one of embodiments 115-161, wherein the analyte is an RNA.

Embodiment 163 is the method of embodiment 162, wherein the RNA is an mRNA.

Embodiment 164 is the method of any one of embodiments 115-161, wherein the analyte is a DNA.

Embodiment 165 is the method of embodiment 164, wherein the DNA is genomic DNA.

Embodiment 166 is a kit comprising: (i) a first restriction endonuclease that cleaves a first restriction endonuclease recognition sequence; (ii) a ligase; and (iii) a first and a second primer, wherein: the first primer comprises: (i) a sequence substantially complementary to a reverse complement of a first adaptor, and (ii) a sequence comprising a first functional domain; and the second primer comprises: (i) a sequence substantially complementary to a sequence from a 5' region of a sequence encoding the constant region of the analyte, and (ii) a sequence comprising a second functional domain.

Embodiment 167 is the kit of embodiment 166, wherein the kit further comprises: a third primer comprising a sequence substantially complementary to the first functional domain; and a fourth primer comprising a sequence substantially complementary to the second functional domain.

Embodiment 168 is the kit of embodiment 166 or 167, wherein the first primer comprises (i) the sequence substantially complementary to the reverse complement of the first adaptor, and (ii) the sequence comprising the first functional domain, in a 3' to 5' direction.

Embodiment 169 is the kit of any one of embodiments 166-168, wherein the second primer comprises (i) the sequence substantially complementary to the sequence from the 5' region of the sequence encoding the constant region of the analyte, and (ii) the sequence comprising the second functional domain, in a 3' to 5' direction.

Embodiment 170 is the kit of any one of embodiments 166-169, wherein the ligase is a DNA ligase.

Embodiment 171 is the kit of embodiment 170, wherein the DNA ligase is T4 ligase.

Embodiment 172 is a method of reversing the orientation of an analyte sequence of a double-stranded member of a nucleic acid library, wherein the double-stranded member of the nucleic acid library comprises a ligation sequence, a barcode, a reverse complement of the first adaptor, an amplification domain, a capture domain, a sequence that is complementary to all or a portion of the sequence encoding the analyte, and a second adaptor, wherein the method comprises: (a) ligating ends of the double-stranded member of the nucleic acid library using the ligation sequence to splint ligation, to generate a circularized double-stranded nucleic acid; and (b) amplifying the circularized double-stranded nucleic acid using a first primer and a second primer to generate a double-stranded nucleic acid product, wherein: the first primer comprises (i) a sequence substantially complementary to the reverse complement of the first adaptor and (ii) a functional domain; and the second primer comprises a sequence substantially complementary to the amplification domain, thereby reversing the orientation of the analyte sequence of the double-stranded member of the nucleic acid library.

Embodiment 173 is the method of embodiment 172, wherein the double-stranded member of the nucleic acid library comprises the ligation sequence, the barcode, the reverse complement of the first adaptor, the amplification domain, the capture domain, the sequence complementary to all or a portion of the sequence encoding an analyte, and the second adaptor, in a 5' to 3' direction.

Embodiment 174 is the method of embodiment 173, wherein the double-stranded member of the nucleic acid library further comprises a unique molecular identifier (UMI) disposed between the barcode and the reverse complement of the first adaptor.

Embodiment 175 is the method of any one of embodiments 172-174, wherein the first primer comprises (i) the sequence substantially complementary to the reverse complement of the first adaptor, and (ii) the sequence comprising the first functional domain, in a 5' to 3' direction.

Embodiment 176 is the method of any one of embodiments 172-175, wherein ligating in step (a) is performed using a ligase.

Embodiment 177 is the method of embodiment 176, wherein the ligase is a DNA ligase.

Embodiment 178 is the method of embodiment 177, wherein the DNA ligase is T4 ligase.

Embodiment 179 is the method of any one of embodiments 172-178, wherein the barcode is a spatial barcode or a cell barcode.

Embodiment 180 is the method of any one of embodiments 172-179, wherein the nucleic acid library is a DNA library.

Embodiment 181 is the method of any one of embodiments 172-179, wherein the nucleic acid library is a cDNA library.

Embodiment 182 is the method of any one of embodiments 172-181, wherein the double-stranded member of the nucleic acid library further comprises a sequence that is complementary to all or a portion of a sequence encoding a 5' untranslated region of an analyte.

Embodiment 183 is the method of any one of embodiments 172-182, wherein the double-stranded member of the nucleic acid library further comprises a sequence that is complementary to all or a portion of a sequence encoding a 3' untranslated region of an analyte.

Embodiment 184 is the method of embodiment 183, wherein the sequence that is complementary to all or a portion of the sequence encoding a 5' untranslated region of the analyte is positioned 5' relative to the sequence that is complementary to all or a portion of the sequence encoding the 3' untranslated region of the analyte.

Embodiment 185 is the method of any one of embodiments 172-184, wherein the double-stranded member of the nucleic acid library comprises one or more exons of the analyte.

Embodiment 186 is the method of embodiment 185, wherein the analyte comprises the sequence that is complementary to all or a portion of the sequence encoding the 5' untranslated region of the analyte, the one or more exons, and the sequence that is complementary to all or a portion of the sequence encoding the 3' untranslated region, in a 5' to 3' direction.

Embodiment 187 is the method of any one of embodiments 172-186, wherein the method further comprises: (c) determining (i) all or a portion of a sequence encoding the analyte or a complement thereof, and (ii) all or a portion of the barcode, or a complement thereof.

Embodiment 188 is the method of embodiment 187, wherein the determining in step (c) comprises sequencing (i) all or a portion of the sequence encoding the analyte or a complement thereof, and (ii) all or a portion of the barcode or a complement thereof.

Embodiment 189 is the method of embodiment 188, wherein the sequencing comprises high throughput sequencing.

Embodiment 190 is the method of embodiment 188, wherein the sequencing is performed using sequence by synthesis, sequence by ligation or sequence by hybridization.

Embodiment 191 is the method of any one of embodiments 188-190, wherein the analyte was released from a biological sample, and the method further comprises: determining a location of the analyte in the biological sample using the determined sequences of (i) and (ii).

Embodiment 192 is the method of any one of embodiments 172-191, further comprising generating the double-stranded member of the nucleic acid library.

Embodiment 193 is the method of embodiment 192, wherein the step of generating the double-stranded member of the nucleic acid library comprises: contacting the analyte with a capture probe comprising the ligation sequence, the barcode, the reverse complement of the first adaptor, the amplification domain, and the capture domain, wherein the capture domain binds specifically to a sequence present in the analyte; extending an end of the capture probe using the analyte specifically bound to the capture domain as a template, thereby generating an extended capture probe; and adding the second adaptor to an end of the extended capture probe, thereby generating the double-stranded member of the nucleic acid library.

Embodiment 194 is the method of embodiment 193, wherein the capture probe comprises the ligation sequence, the barcode, the reverse complement of the first adaptor, the amplification domain, and the capture domain in a 5' to a 3' direction.

Embodiment 195 is the method of embodiment 193 or 194, wherein a 3' end of the capture probe is extended.

Embodiment 196 is the method of any one of embodiments 193-195, wherein the second adapter is added to a 5' end of the extended capture domain.

Embodiment 197 is the method of any one of embodiments 191-196, wherein the biological sample is a tissue sample, a tissue section or a fixed tissue section.

Embodiment 198 is the method of embodiment 197, wherein the fixed tissue section is formalin-fixed paraffin-embedded tissue section or the tissue section is a fresh, frozen tissue section.

Embodiment 199 is the method of any one of embodiments 172-198, wherein the analyte is an RNA.

Embodiment 200 is the method of embodiment 199, wherein the RNA is an mRNA.

Embodiment 201 is the method of any one of embodiments 172-200, wherein the analyte is a DNA.

Embodiment 202 is the method of embodiment 201, wherein the DNA is genomic DNA.

Embodiment 203 is the method of any one of embodiments 172-202, wherein the analyte is a nucleic acid encoding an immune cell receptor.

Embodiment 204 is the method of embodiment 203, wherein the immune cell receptor is a B-cell receptor.

Embodiment 205 is the method of embodiment 204, wherein the B cell receptor is one of an immunoglobulin kappa light chain, an immunoglobulin lambda chain, and/or an immunoglobulin heavy chain.

Embodiment 206 is the method of embodiment 203, wherein the immune cell receptor is a T cell receptor.

Embodiment 207 is the method of embodiment 206, wherein the T cell receptor is one or both of a T cell receptor alpha chain and a T cell receptor beta chain.

Embodiment 208 is a kit comprising: (i) a first restriction endonuclease that cleaves a first restriction endonuclease recognition sequence; (ii) a ligase; and (iii) a first and a second primer, wherein: the first primer comprises: (i) a sequence substantially complementary to a reverse complement of a first adaptor, and (ii) a functional domain; and the second primer comprises a sequence substantially complementary to the amplification domain.

Embodiment 209 is the kit of embodiment 208, wherein the kit further comprises: a third primer comprising a sequence substantially complementary to the functional domain; and a fourth primer comprising a sequence substantially complementary to a reverse complement of the amplification domain.

Embodiment 210 is the kit of embodiment 208 or 209, wherein the first primer comprises (i) the sequence substantially complementary to the reverse complement of the first adaptor, and (ii) the sequence comprising the functional domain, in a 3' to 5' direction.

Embodiment 211 is the kit of any one of embodiments 208-210, wherein the ligase is a DNA ligase.

Embodiment 212 is the kit of embodiment 211, wherein the DNA ligase is T4 ligase.

Embodiment 213 is a method for removing all or a portion of a sequence encoding an analyte from a double-stranded member of a nucleic acid library, wherein the double-stranded member of the nucleic acid library comprises: a first adaptor, a barcode, a capture domain, a sequence that is complementary to all or a portion of the sequence encoding the analyte, and a second adaptor, wherein the method comprises: (a) adding to each end of the double-stranded member of the nucleic acid library a first restriction endonuclease recognition sequence; (b) contacting the double-stranded member of the nucleic acid library of step (a) with a first restriction endonuclease that cleaves the first restriction endonuclease recognition sequence at each end of the double-stranded member of the nucleic acid library; (c) ligating ends of the double-stranded member of the nucleic acid library of step (b) to generate a first double-stranded circularized nucleic acid; (d) amplifying the first double-stranded circularized nucleic acid using a first and a second primer to generate a first double-stranded nucleic acid product, wherein: the first primer comprises: (i) a sequence substantially complementary to a 3' region of the sequence encoding the analyte and (ii) a second restriction endonuclease recognition sequence; and the second primer comprises: (i) a sequence substantially complementary to a sequence from a 5' region of the sequence encoding the analyte, and (ii) the second restriction endonuclease recognition sequence; (e) contacting the first double-stranded nucleic acid product with a second restriction endonuclease that cleaves the second restriction endonuclease recognition sequence at each end of the first double-stranded nucleic acid product; (f) ligating ends of the first double-stranded nucleic acid product of step (e) to generate a second double-stranded circularized nucleic acid; and (g) amplifying the second double-stranded circularized nucleic acid using a third primer comprising a sequence that is substantially complementary to the first adapter and a fourth primer comprising a sequence that is substantially complementary to the second adapter, to generate a version of the double-stranded member of the nucleic acid library lacking all or a portion the sequence encoding the analyte.

Embodiment 214 is a method for removing all or a portion of a sequence encoding an analyte from a double-stranded member of a nucleic acid library, wherein the double-stranded member of the nucleic acid library comprises: a first adaptor, a barcode, a capture domain, a sequence that is complementary to all or a portion of the sequence encoding the analyte, and a second adaptor, wherein the method comprises: (a) adding to each end of the double-stranded member of the nucleic acid library a first restriction endonuclease recognition sequence; (b) contacting the double-stranded member of the nucleic acid library of step (a) with a first restriction endonuclease that cleaves the first restriction endonuclease recognition sequence at each end; (c) ligating ends of the double-stranded member of the nucleic acid library of step (b) to generate a first-double-stranded nucleic acid circularized nucleic acid; and (d) amplifying the double-stranded circularized nucleic acid using a first primer and a second primer to generate a version of the double-stranded member of the nucleic acid library lacking all, or a portion of, the sequence encoding the analyte, wherein: the first primer comprises: (i) a sequence substantially complementary to a sequence from a 3' region of the sequence encoding the analyte, and (ii) a sequence comprising a first functional domain; and the second primer comprises: (i) a sequence substantially complementary to a sequence from a 5' region of the sequence encoding the analyte, and (ii) a sequence comprising a second functional domain.

Embodiment 215 is a method for removing all or a portion of the sequence encoding an analyte from a double-stranded member of a nucleic acid library, wherein the double-stranded member of the nucleic acid library comprises a ligation sequence, a barcode, a reverse complement of a first adaptor, a capture domain, a sequence that is complementary to all or a portion of the sequence encoding the analyte, and a second adaptor, wherein the method comprises: ligating ends of the double-stranded member using the ligation sequence to splint ligation, to generate a circularized double-stranded nucleic acid; amplifying the circularized double-stranded nucleic acid using a first primer and a second primer to generate a version of the double-stranded member of the nucleic acid library lacking all, or a portion of, the sequence encoding the analyte, wherein: the first primer comprises: (i) a sequence substantially complementary to the reverse complement of the first adaptor and (ii) a first functional domain; and the second primer comprises: (i) a sequence substantially complementary to a sequence from a 5' region of the sequence encoding the analyte, and (ii) a second functional domain.

EXAMPLES

Example 1: Removal of a Portion of a Member of a Nucleic Acid Library Via Circularization FIGS. 2A-I show an exemplary nucleic acid library preparation method to remove a portion of an analyte sequence via double circularization of a member of a nucleic acid library. FIG. 2A shows an exemplary member of a nucleic acid library including, in a 5' to 3' direction, a first adaptor (e.g., primer sequence R1, pR1 (e.g., Read 1)), a barcode (e.g., a spatial barcode or a cell barcode), a unique molecular identifier (UMI), a capture domain (e.g., poly(T) VN sequence), a sequence complementary to an analyte (C, J, D and V), and a second adaptor (e.g., template switching oligonucleotide sequence (TSO)). For purposes of this example an analyte including a constant region (C) and V(D)J sequence are shown, however, the methods described herein can be equally applied to other analyte sequences in a nucleic acid library.

FIG. 2B shows the exemplary member of a nucleic acid library where additional sequences can be added to both the 3' and 5' ends of the nucleic acid member (shown as a X and Y) via a PCR reaction. The additional sequences added can include a recognition sequence for a restriction enzyme (e.g., restriction endonuclease). The restriction recognition sequence can be for a rare restriction enzyme.

The exemplary member of the nucleic acid library shown in FIG. 2B, can be digested with a restriction enzyme to generate sticky ends shown in FIG. 2C (shown as triangles) and can be intramolecularly circularized by ligation to generate the circularized member of the nucleic acid library shown in FIG. 2D. The ligation can be performed with a DNA ligase. The ligase can be T4 ligase.

A primer pair can be hybridized to a circularized nucleic acid member, where a first primer hybridizes to a 3' portion of a sequence encoding the constant region (C) and includes a second restriction enzyme (e.g., restriction endonuclease) sequence that is non-complementary to the analyte sequence, and where a second primer hybridized to a 5' portion of a sequence encoding the constant region (C), and where the second primer includes a second restriction enzyme sequence (FIG. 2E). The first primer and the second primer can generate a linear amplification product (e.g., a first double-stranded nucleic acid product) as shown in FIG. 2F, which includes the second restriction enzyme recognition sequences (shown as X and Y end sequences). The linear amplification product (FIG. 2F) can be digested with a second restriction enzyme to generate sticky ends and can be intramolecularly ligated with a ligase (e.g., T4 DNA ligase) to generate a second double-stranded circularized nucleic acid product as shown in FIG. 2G.

The second double-stranded circularized nucleic product (FIG. 2G) can be amplified with a third primer, pR1, substantially complementary to the first adaptor (e.g., Read 1) sequence and a fourth primer substantially complementary to the second adapter (e.g., TSO) as shown in FIG. 2H primer to generate a version of the double-stranded member of the nucleic acid library lacking all, or a portion of, the sequence encoding the constant region (C) of the analyte (FIG. 2I).

The resulting double-stranded member of the nucleic acid library lacking all or a portion of the constant region can undergo standard library preparation methods, such as library preparation methods used in single-cell or spatial analyses. For example, the double-stranded member of the nucleic acid library lacking all, or a portion of, the sequence encoding the constant region of the analyte can be fragmented, followed by end repair, a-tailing, adaptor ligation, and/or additional amplification (e.g., PCR). The fragments can then be sequenced using, for example, paired-end sequencing using TruSeq Read 1 and TruSeq Read 2 as sequencing primer sites or any other sequencing method described herein.

As a result of the methods described in this Example, sequences can be determined from regions more than about 1 kb away from the end of an analyte (e.g., 3' end) and can link such a sequence to a barcode sequence (e.g., a spatial barcode, a cell barcode) in library preparation methods (e.g., sequencing preparation). For purposes of this example an analyte including a constant region (C) and V(D)J sequences are shown, however, the methods described herein can be equally applied to other analyte sequences in a nucleic acid library.

Example 2: Removal of a Portion of a Member of a Nucleic Acid Library Via Single Circularization In this Example an exemplary member of a nucleic acid library can be prepared as shown in FIGS. 2A-D to generate a first double-stranded circularized nucleic acid product (FIG. 2D) as previously described. A primer pair can be contacted with the double-stranded circularized nucleic acid produce with a first primer that can hybridize to a sequence from a 3' region of the sequence encoding the constant region of the analyte and a sequence including a first functional domain (e.g., P5). The second primer can hybridize to a sequence from a 5' region of the sequence encoding the constant region of the analyte, and includes a sequence including a second functional domain (shown as "X") as shown in FIG. 3A.

Figures 3A, 3B:
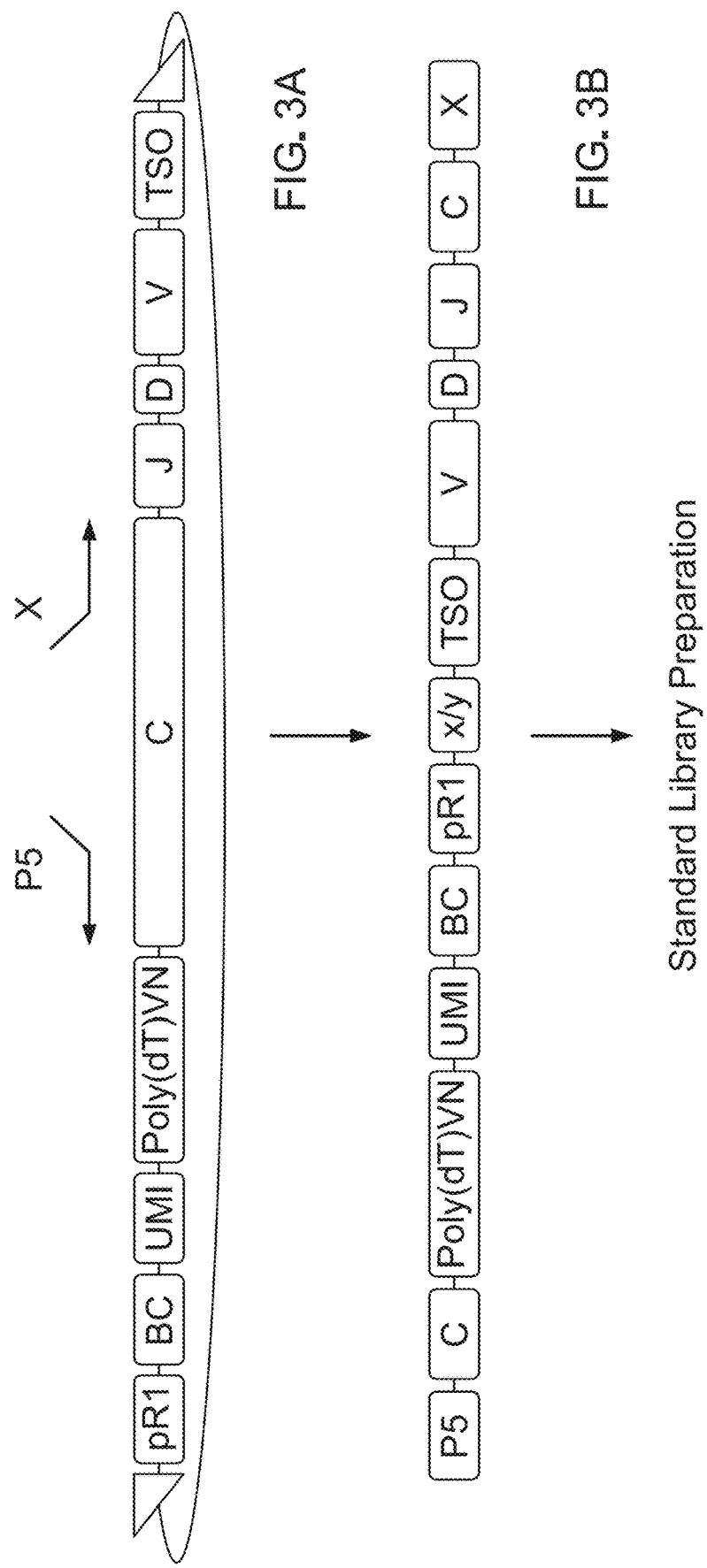
FIGS. 3A-C show an exemplary nucleic acid library preparation workflow.

Amplification of the double-stranded circularized nucleic acid product results in a linear product as shown in FIG. 3B, where all, or a portion of, the constant region (C) is removed. The first functional domain can include a sequencer specific flow cell attachment sequence (e.g., P5). The second functional domain can include an amplification domain such as a primer sequence to amplify the nucleic acid library prior to further sequencing preparation.

Figure 3C:
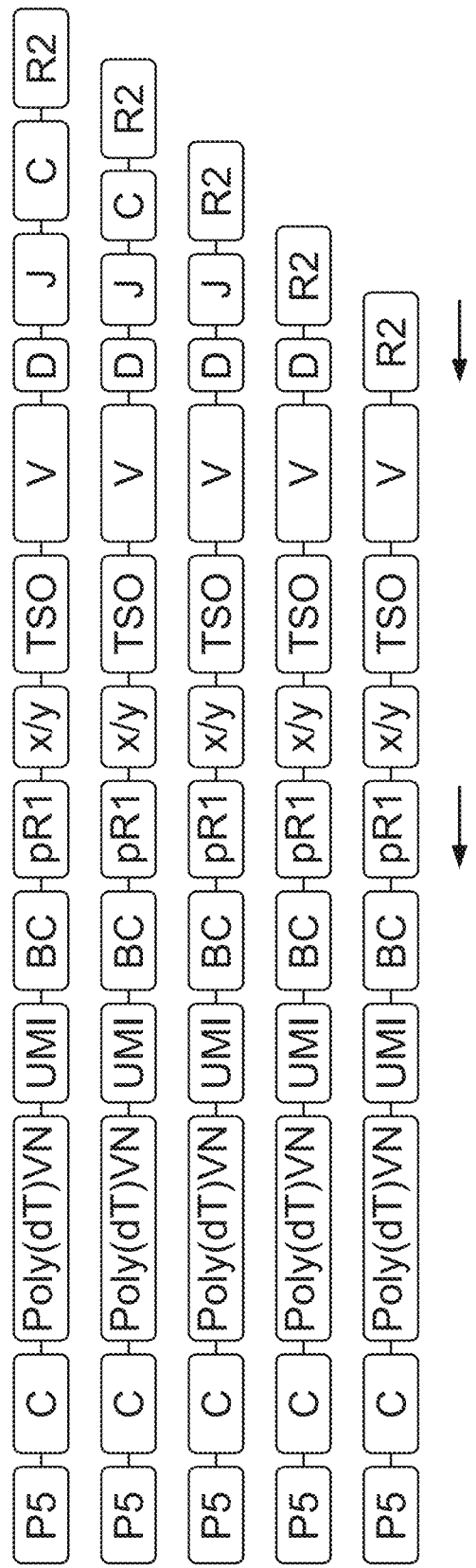

The resulting double-stranded member of the nucleic acid library lacking all or a portion of the constant region can undergo standard library preparation methods, such as library preparation methods used in single-cell or spatial analyses. For example, the double-stranded member of the nucleic acid library lacking all, or a portion of, the sequence encoding the constant region of the analyte can be fragmented, followed by end repair, A-tailing, adaptor ligation, and/or amplification (e.g., PCR) (FIG. 3C). The fragments can then be sequenced using, for example, paired-end sequencing using TruSeq Read 1 and TruSeq Read 2 as sequencing primer sites (FIG. 3C, arrows), or any other sequencing method described herein.

In this Example, after standard library preparation methods described herein, a different sequencing primer for the first adaptor (e.g., Read 1) is used since the orientation of the first adaptor (e.g., Read 1) sequence will be reversed.

As a result of the methods described in this Example, sequences can be determined from regions more than about 1 kb away from the end of an analyte (e.g., 3' end) and can link such a sequence to a barcode sequence (e.g., a spatial barcode, a cell barcode) in further library preparation methods (e.g., sequencing preparation). For purposes of this example an analyte including a constant region (C) and V(D)J sequence are shown, however, the methods described herein can be applied to other analyte sequences in a nucleic acid library as well.

Example 3: Removal of a Portion of a Member of a Nucleic Acid Library Via Single Circularization FIGS. 4A-B show an exemplary nucleic acid library preparation method to remove all or a portion of a constant sequence of an analyte from a member of a nucleic acid library via circularization. FIGS. 4A and 4B shows an exemplary member of a nucleic acid library including, in a 5' to 3' direction, a ligation sequence, a barcode sequence, a unique molecular identifier, a reverse complement of a first adaptor (e.g., primer sequence pR1 (e.g., Read 1)), a capture domain, a sequence complementary to the captured analyte sequence, and a second adapter (e.g., TSO sequence). The ends of the double-stranded nucleic acid can be ligated together via a ligation reaction where the ligation sequence splints the ligation to generate a circularized double-stranded nucleic acid as shown in FIG. 4B.

The circularized double-stranded nucleic acid can be amplified with a pair of primers to generate a linear nucleic acid product lacking all or a portion of the constant region of the analyte (FIGS. 4B and 4C). The first primer can include a sequence substantially complementary to the reverse complement of the first adaptor and a first functional domain. The first functional domain can be a sequencer specific flow cell attachment sequence (e.g., P5). The second primer can include a sequence substantially complementary to a sequence from a 5' region of the sequence encoding the constant region of the analyte, and a second functional domain. The second functional domain can include an amplification domain such as a primer sequence to amplify the nucleic acid library prior to further sequencing preparation.

Figure 4D:
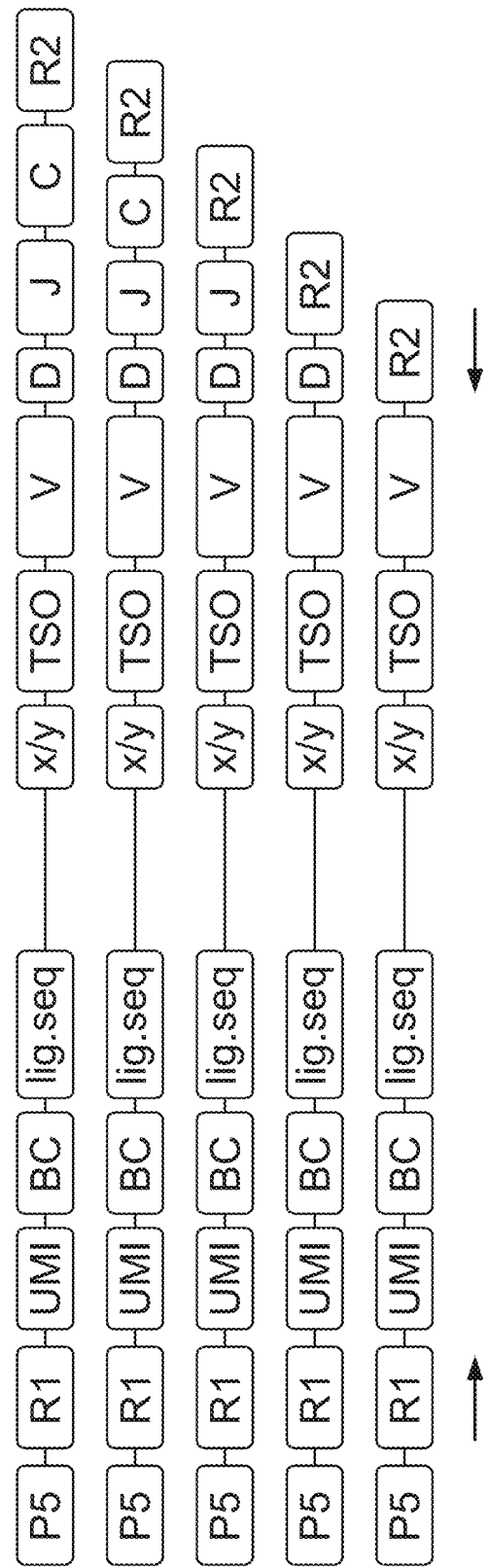

The resulting double-stranded member of the nucleic acid library lacking all or a portion of the constant region can undergo standard library preparation methods, such as library preparation methods used in single-cell or spatial analyses. For example, the double-stranded member of the nucleic acid library lacking all, or a portion of, the sequence encoding the constant region of the analyte can be fragmented, followed by end repair, A-tailing, adaptor ligation, and/or amplification (e.g., PCR) (FIG. 4C). The fragments can then be sequenced using, for example, paired-end sequencing using TruSeq Read 1 and TruSeq Read 2 as sequencing primer sites, or any other sequencing method described herein (FIG. 4D).

In this Example, after standard library preparation methods described herein, standard sequencing primers can be used since the orientation of Read 1 will be in the proper orientation for sequencing primer pR1.

As a result of the methods described in this Example, sequences can be determined from regions more than about 1 kb away from the end of an analyte (e.g., 3' end) and can link such a sequence to a barcode sequence (e.g., a spatial barcode, a cell barcode) in further library preparation methods (e.g., sequencing preparation). For purposes of this example an analyte including a constant region (C) and V(D)J sequence are shown, however, the methods described herein can be applied to other analyte sequences in a nucleic acid library as well.

Example 4: Reversal of the Orientation of an Analyte Sequence in a Member of a Nucleic Acid Library FIGS. 5A-B show an exemplary nucleic acid library method to reverse the orientation of an analyte sequence in a member of a nucleic acid library. FIG. 5A shows an exemplary member of a nucleic acid library including, in a 5' to 3' direction, a ligation sequence, a barcode (e.g., a spatial barcode or a cell barcode), unique molecular identifier, a reverse complement of a first adaptor, an amplification domain, a capture domain, a sequence complementary to an analyte, and a second adapter.

The ends of the double-stranded nucleic acid can be ligated together via a ligation reaction where the ligation sequence splints the ligation to generate a circularized double-stranded nucleic acid also shown in FIG. 5A.

The circularized double-stranded nucleic acid can be amplified to generate a linearized double-stranded nucleic acid product, where the orientation of the analyte is reversed such that the 5' sequence (e.g., 5' UTR) is brought in closer proximity to the barcode (e.g., a spatial barcode or a cell barcode) (FIG. 5B). The first primer includes a sequence substantially complementary to the reverse complement of the first adaptor and a functional domain. The functional domain can be a sequencer specific flow cell attachment sequence (e.g., P5). The second primer includes a sequence substantially complementary to the amplification domain.

The resulting double-stranded member of the nucleic acid library including a reversed analyte sequence (e.g., the 5' end of the analyte sequence is brought in closer proximity to the barcode) can undergo standard library preparation methods, such as library preparation methods used in single-cell or spatial analyses. For example, the double-stranded member of the nucleic acid library lacking all, or a portion of, the sequence encoding the constant region of the analyte can be fragmented, followed by end repair, A-tailing, adaptor ligation, and/or amplification (e.g., PCR) (FIG. 5C). The fragments can then be sequenced using, for example, paired-end sequencing using TruSeq Read 1 and TruSeq Read 2 as sequencing primer sites, or any other sequencing method described herein.

As a result of the methods described in this Example, sequences from the 5' end of an analyte will be included in sequencing libraries (e.g., paired end sequencing libraries). Any type of analyte sequence in a nucleic acid library can be prepared by the methods described in this Example (e.g., reversed).

What is claimed is:

1. A method for removing all or a portion of a nucleic acid analyte sequence from a double-stranded member of a nucleic acid library, wherein a single-strand of the double-stranded member of the nucleic acid library comprises: a ligation sequence, a barcode, a reverse complement of a first adaptor, a capture domain, a sequence that is complementary to all or a portion of the nucleic acid analyte sequence, and a second adaptor, wherein the method comprises:
    (a) ligating ends of the double-stranded member using the ligation sequence to generate a circularized double-stranded nucleic acid;

(b) amplifying the circularized double-stranded nucleic acid using a first primer and a second primer to generate a double-stranded member of the nucleic acid library lacking all or a portion of the nucleic acid analyte sequence, wherein:
the first primer comprises: (i) a sequence substantially complementary to the reverse complement of the first adaptor and (ii) a first functional domain; and
the second primer comprises: (i) a sequence substantially complementary to a sequence from a 5' region of the nucleic acid analyte sequence, and (ii) a second functional domain.

2. The method of claim 1, wherein the double-stranded member of the nucleic acid library comprises the ligation sequence, the barcode, the reverse complement of the first adaptor, the capture domain, the sequence complementary to all or a portion of the nucleic acid analyte sequence, and the second adaptor, in a 5' to 3' direction.

3. The method of claim 2, wherein the single strand of the double-stranded member of the nucleic acid library further comprises a unique molecular identifier (UMI) disposed between the barcode and the reverse complement of the first adaptor.

4. The method of claim 1, wherein the first primer comprises: (i) the sequence substantially complementary to the reverse complement of the first adaptor, and (ii) the sequence comprising the first functional domain, in 3' to 5' direction; and
wherein the second primer comprises (i) the sequence substantially complementary to a sequence of the 5' region of the nucleic acid analyte sequence and (ii) the sequence comprising the second functional domain, in a 3' to 5' direction.

5. The method of claim 1, wherein ligating in step (a) is performed using a DNA ligase, optionally wherein the DNA ligase is T4 ligase.

6. The method of claim 1, wherein the barcode is a spatial barcode or a cell barcode.

7. The method of claim 1, wherein the nucleic acid library is a DNA library or a cDNA library.

8. The method of claim 1, wherein the nucleic acid analyte sequence encodes an immune cell receptor.

9. The method of claim 8, wherein the nucleic acid analyte sequence encodes a constant region of the immune cell receptor.

10. The method of claim 9, wherein the nucleic acid analyte sequence further encodes a variable region of the immune cell receptor.

11. The method of claim 10, wherein the sequence that is complementary to all or a portion of the nucleic acid analyte sequence encoding the constant region of the immune cell receptor is positioned 5' relative to the sequence that is complementary to all or a portion of the nucleic acid analyte sequence encoding the variable region of the immune cell receptor.

12. The method of claim 10, wherein the sequence that is complementary to all or a portion of the nucleic acid analyte sequence encoding the constant region of the immune cell receptor is positioned 3' relative to the sequence that is complementary to all or a portion of the nucleic acid analyte sequence encoding the variable region of the immune cell receptor.

13. The method of claim 10, wherein the immune cell receptor is a B cell receptor.

14. The method of claim 13, wherein the B cell receptor comprises an immunoglobulin kappa light chain and wherein the variable region comprises a CDR3 of the immunoglobulin kappa light chain, or
wherein the variable region further comprises one or both of CDR1 and CDR2 of the immunoglobulin kappa light chain, or
wherein the variable region further comprises a full-length variable domain of the immunoglobulin kappa light chain.

15. The method of claim 13, wherein the B cell receptor comprises an immunoglobulin lambda light chain and wherein the variable region comprises a CDR3 of the immunoglobulin lambda light chain, or
wherein the variable region further comprises one or both of CDR1 and CDR2 of the immunoglobulin lambda light chain, or
wherein the variable region further comprises a full-length variable domain of the immunoglobulin lambda light chain.

16. The method of claim 13, wherein the B cell receptor comprises an immunoglobulin heavy chain and wherein the variable region comprises a CDR3 of the immunoglobulin heavy chain, or wherein the variable region further comprises one or both of CDR1 and CDR2 of the immunoglobulin heavy chain, or wherein the variable region further comprises a full-length variable domain of the immunoglobulin heavy chain.

17. The method of claim 10, wherein the immune cell receptor is a T cell receptor.

18. The method of claim 17, wherein the T cell receptor comprises a T cell receptor alpha chain and wherein the variable region comprises a CDR3 of the T cell receptor alpha chain, or
wherein the variable region further comprises one or both of CDR1 and CDR2 of the T cell receptor alpha chain, or
wherein the variable region further comprises a full-length variable domain of the T cell receptor alpha chain.

19. The method of claim 17, wherein the T cell receptor comprises a T cell receptor beta chain and wherein the variable region comprises a CDR3 of the T cell receptor beta chain, or
wherein the variable region further comprises one or both of CDR1 and CDR2 of the T cell receptor beta chain, or
wherein the variable region further comprises a full-length variable domain of the T cell receptor beta chain.

20. The method of claim 9, wherein the method further comprises amplifying the double-stranded member of the nucleic acid library lacking all, or a portion of, the sequence of the nucleic acid analyte sequence encoding the constant region of the immune cell receptor using a third primer and fourth primer, wherein:
the third primer is substantially complementary to the first functional domain, and
the fourth primer is substantially complementary to the second functional domain.

21. The method of claim 10, wherein the method further comprises:
determining (i) all or a portion of the sequence of the nucleic acid analyte sequence encoding the variable region of the immune cell receptor or complement thereof, and (ii) the sequence of the barcode or complement thereof.

22. The method of claim 21, wherein the determining the sequence comprises sequencing (i) all or a portion of the sequence of the nucleic acid analyte sequence encoding the variable region of the immune cell receptor or complement thereof, and (ii) the sequence of the barcode or a complement thereof.

23. The method of claim 21, wherein the nucleic acid analyte sequence was released from a biological sample, and the method further comprises:
determining a location of the nucleic acid analyte sequence in the biological sample using the determined sequence of (i) and (ii).

24. The method of claim 1, further comprising generating the double-stranded member of the nucleic acid library.

25. The method of claim 24, wherein the step of generating the double-stranded member of the nucleic acid library comprises:
contacting the nucleic acid analyte sequence with a capture probe comprising the ligation sequence, the barcode, the reverse complement of the first adaptor, the capture domain, wherein the capture domain hybridizes to a sequence present in the nucleic acid analyte sequence;
extending an end of the capture probe using the nucleic acid analyte sequence hybridized to the capture domain as a template, thereby generating an extended capture probe; and
adding the second adaptor to an end of the extended capture probe, thereby generating the double-stranded member of the nucleic acid library.

26. The method of claim 25, wherein the capture probe comprises the ligation sequence, the barcode, the reverse complement of the first adaptor, and the capture domain in a 5' to a 3' direction.

27. The method of claim 25, wherein a 3' end of the capture probe is extended.

28. The method of claim 25, wherein the second adapter is added to a 3' end of the extended capture probe.

29. The method of claim 23, wherein the biological sample is a tissue sample or a tissue section, and optionally, wherein the tissue section is a formalin-fixed paraffin-embedded tissue section or the tissue section is a fresh, frozen tissue section.

30. The method of claim 1, wherein the nucleic acid analyte sequence is an RNA, mRNA, DNA, or genomic DNA.

* * * * *